(12) United States Patent
Meyers et al.

(10) Patent No.: US 11,358,994 B2
(45) Date of Patent: Jun. 14, 2022

(54) FATTY ACID MODIFIED HUMAN EPIDERMAL GROWTH FACTOR

(71) Applicant: Saint Louis University, St. Louis, MO (US)

(72) Inventors: Marvin J. Meyers, Wentzville, MO (US); David C. Wood, Wildwood, MO (US); Stacy D. Arnett, St. Louis, MO (US); Matthew P. Yates, Dardenne Prairie, MO (US); Peter G. Ruminski, Wildwood, MO (US)

(73) Assignee: Saint Louis University, St. Louis, MO (US)

( * ) Notice: Subject to any disclaimer, the term of this patent is extended or adjusted under 35 U.S.C. 154(b) by 0 days.

(21) Appl. No.: 16/633,467

(22) PCT Filed: Jul. 25, 2018

(86) PCT No.: PCT/US2018/043598
§ 371 (c)(1),
(2) Date: Jan. 23, 2020

(87) PCT Pub. No.: WO2019/023295
PCT Pub. Date: Jan. 31, 2019

(65) Prior Publication Data
US 2020/0190157 A1 Jun. 18, 2020

Related U.S. Application Data

(60) Provisional application No. 62/537,808, filed on Jul. 27, 2017.

(51) Int. Cl.
| | | |
|---|---|---|
| C07K 14/485 | (2006.01) | |
| A61K 38/00 | (2006.01) | |
| A61P 1/12 | (2006.01) | |
| A61K 9/00 | (2006.01) | |

(52) U.S. Cl.
CPC .......... *C07K 14/485* (2013.01); *A61K 9/0019* (2013.01); *A61P 1/12* (2018.01); *A61K 38/00* (2013.01); *C07K 2319/21* (2013.01); *C07K 2319/50* (2013.01)

(58) Field of Classification Search
None
See application file for complete search history.

(56) References Cited

U.S. PATENT DOCUMENTS

| | | | | |
|---|---|---|---|---|
| 5,070,188 A | * | 12/1991 | Njieha | ............... C07K 14/485 530/324 |
| 8,945,897 B2 | | 2/2015 | Siekmann et al. | |
| 9,708,383 B2 | | 7/2017 | Madsen et al. | |
| 2004/0136952 A1 | * | 7/2004 | Bhaskaran | ........... A61K 38/212 424/85.1 |
| 2004/0266682 A1 | * | 12/2004 | Cruz | ............... A61K 38/1808 514/12.3 |
| 2008/0249008 A1 | * | 10/2008 | Cochran | ............... A61P 25/00 514/1.1 |
| 2010/0022446 A1 | | 1/2010 | Wulff et al. | |
| 2014/0255504 A1 | | 9/2014 | Du Plessis et al. | |
| 2016/0008452 A1 | | 1/2016 | Kickhoefer et al. | |
| 2016/0074526 A1 | | 3/2016 | Bilodeau et al. | |
| 2017/0107255 A1 | * | 4/2017 | Holder | ............... A61P 9/04 |

FOREIGN PATENT DOCUMENTS

| | | |
|---|---|---|
| CN | 106084066 | 6/2016 |
| JP | 02115118 | 4/1990 |
| WO | WO 2012/087838 | 6/2012 |
| WO | WO 2017/121850 | * 7/2017 |

OTHER PUBLICATIONS

Brown GL, Curtsinger LJ, White M, et al. "Acceleration of Tensile Strength of Incisions Treated With EGF and TGF-beta," Ann Surg 1988;208,788-94.
Brown BW, Mattner PE, Panaretto BA, et al. "Effect of Mouse Epidermal Growth Factor on Plasma Concentrations of LH, FSH and Testosterone in Rams," J Reprod Fertil 1989;87,649-55.
Bollu et al. "Intracellular Activation of EGFR by Fatty Acid Synthase Dependent Palmitoylation," Oncotarget, Sep. 12, 2015, vol. 6, No. 33, pp. 34992-35003.
Calnan DP, Fagbemi A, Berlanga-Acosta J, et al. "Potency and Stability of C Terminal Truncated Human Epidermal Growth Factor," Gut 2000;47(5),622-7.
Chaet MS, Arya G, Ziegler MM, et al. "Epidermal Growth Factor Enhances Intestinal Adaptation After Massive Small Bowel Resection," J Pedriatr Surg 1994;29,1035-8.
Fiore NF, Ledniczky G, Liu Q et al. "Comparison of interleukin-11 and Epidermal Growth Factor on Residual Small Intestine After Massive Small Bowel Resection," J Pediatr Surg 1998:33,24-9.
Garg M, Jones RM, Vaughn RB, Testro AG. "Intestinal Transplantation: Current Status and Future Directions," J Gastroenterol Hepatol 2011;26(8),1221-1228.
Gregory H, Thomas CE, Young JA, et al. "The Contribution of the C-terminal Undecapeptide Sequence of Urogastrone-Epidermal Growth Factor to its Biological Action," Regul Pept 1988;22:217-26.
Helmrath MA, Shin CE, Erwin CR, et al. "The EGF\EGF-Receptor Axis Modulates Enterocyte Apoptosis During Intestinal Adaptation," J Surg Res 1998;77:17-22.
Herper M, "Inside the pricing of a $300,000-a-year drug. Forbes 2013" http://onforb.es/XmAB4S.
Huang HW, Mohan SK, Yu C, et al. "The NMR Solution Structure of Human Epidermal Growth Factor (hEGF) at Physiological pH and its Interactions with Suramin," Biochem Biophys Res Commun 2010;402,705-10.

(Continued)

*Primary Examiner* — Marianne P Allen
(74) *Attorney, Agent, or Firm* — Parker Highlander PLLC

(57) ABSTRACT

The disclosure provides for new epidermal growth factor (EGF)-based reagents that have been modified by fatty acid conjugation. Method of using such agents to treatment Short Bowel Syndrome (SBS) are also described.

2 Claims, 2 Drawing Sheets
Specification includes a Sequence Listing.

(56) References Cited

OTHER PUBLICATIONS

International Search Report for PCT/US18/43598, dated Nov. 26, 2018,5pgs.

Kim et al., "Hyaluronate-Epidermal Growth Factor Conjugate for Skin Wound Healing and Regeneration," Biomacromolecules, 2016, 17(11), 3694-3705.

LaRosa C, Baluarte HJ, Meyers KE. "Outcomes in Pediatric Solid-Organ Transplantation," Pediatr Transplant 2011;15(2):128-141.

Lee H, Jang IH, Ryu SH, et al. "N-terminal Site-Specific mono-PEGylation of Epidermal Growth Factor," Pharm Res 2003;20:818-25.

Lee JY, Yoon CS, IY Chung IY, et al. "Scale-up Process of Expression and Renaturation of Recombinant Human Epidermal Growth Factor from *Escherichia coli* Inclusion Bodies," Biotechnol Applied Biochem2000;31,245-8.

Levemir™ [package insert]. Bagsvaerd, Denmark: Novo Nordisk A/S;2015.

McMellen ME, Wakeman D, Longshore SW, et al. "Growth Factors: Possible Roles for Clinical Management of the Short Bowel Syndrome," Semin Pediatr Surg 2010;19:35-43.

Mills BJ, Mu, Q, Krause ME, et al. "claMP Tag: A Versatile Inline Metal-Binding Platform Based on the Metal Abstraction Peptide," Bioconj Chem 2014;25,1103-11.

Na et al., "Effect of Molecular Size of PEGylated Recombinant Human Epidermal Growth Factor on the Biological Activity and Stability in Rat Wound Tissue," Pharmaceutical Development and Technology, 2006, 11(4), 513-519.

Navarro MD, Gleason WA, Rhoads JM, et al. "Short Bowel Syndrome: Epidemiology, Pathophysiology, and Adaptation," Neo Rev 2009;10(7),e330-e338.

O'Loughlin E, Winter M, Shun A, et al. "Structural and Functional Adaptation Following Jejunal Resection in Rabbits: Effect of Epidermal Growth Factor," Gastroenterology 1994;107,87-93.

Ong DE, Brady RN. "Synthesis of Ceramides Using N-hydroxysuccinimide Esters," Journal of Lipid Research 1972;13(6),819-22.

Park et al., "Epidermal Growth Factor (EGF) Receptor Targeted Delivery of PEGylated Adenovirus," Biochemical and Biophysical Research Communications, 2008, 366(3), 769-774.

Pereira et al. "New Growth Factor Therapies Aimed at Improving Intestinal Adaptation in Short Bowel Syndrome," J Gastroenterol Hepatol, May 24, 2006, vol. 21, Issue 6, pp. 932-940.

Playford RJ, Hanby AM, Gschmeissner S, et al. "The Epidermal Growth Factor Receptor (EGF-R) Is Present on the Basolateral, but Not the Apical, Surface of Enterocytes in the Human Gastrointestinal Tract," Gut 1996;39(2),262-6.

Reagan-Shaw et al., "Dose Translation From Animal to Human Studies Revisited," Faseb J., 22(3):659-661, 2008.

Ritz D, Beckwith J. "Roles of Thiol-Redox Pathways in Bacteria," Ann Rev Microbiol 2001;55,21-48.

Sheng G, Guo J, Warner BW. "Epidermal Growth Factor Receptor Signaling Modulates Apoptosis via p38alpha MAPK-dependent Activation of Bas in Intestinal Epithelial Cells," Am J Physiol Gastrointest Liver Physiol 2007;293,G599-606.

Short Bowel Syndrome Foundation, Inc. website; https://www.shortbowelfoundation.org/, last accessed Oct. 7, 2015.

Sigalet DL, Martin GR, Butzner JD, et al. "A Pilot Study of the Use of Epidermal Growth Factor in Pediatric Short Bowel Syndrome," J Pediatr Surg 2005;40:763-8.

Simpson RJ, Smith JA, Moritz RL, et al. "Rat Epidermal Growth Factor: Complete Amino Acid Sequence. Homology With the Corresponding Murine and Human Proteins; Isolation of a Form Truncated at Both Ends With Full in Vitro Biological Activity," Eur J Biochem 1985;153,629-37.

Sizemore N, Wright DS, Mueller WT, et al. "Impact of Receptor Downregulation on Clearance of Two Human EGFs With Different Receptor Binding Activity," Peptides 1996;17:1229-36.

Squires RH, Duggan C, Teitelbaum DH et al. "Natural History of Pediatric Intestinal Failure: Initial Report From the Pediatric Intestinal Failure Consortium," J Pediar 2012;161(4):723-728.

Stern LE, Falcone RA, Huang F, et al. "Epidermal Growth Factor Alters the Bax:bcl-W Ratio Following Massive Small Bowel Resection," J Surg Res 2000;91,38-42.

Sullivan PB, Lewindon PJ, Chang C, et al. "Intestinal Mucosa Remodeling by Recombinant Human Epidermal Growth factor(1-48) in Neonates With Severe Necrotizing Enterocolitis," J Pediatr Surg 2007;42,462-9.

Takeda press release Jun. 14, 2014; https://www.takeda.com/news/2014/20140616_6605.html, last accessed Oct. 7, 2015.

Thompson JS. "Epidermal Growth Factor and the short Bowel Syndrome," J Parenteral Enteral Nutrition 1999;23(5),S113-6.

Varewijck AJ, Goudzwaard JA, Brugts, MP, et al. "Insulin Glargine is More Potent in Activating the Human IGF-I Receptor than Human Insulin and Insulin Detemir," Growth Hormone IGF Res 2010;20(6),427-431.

Victoza™ [package insert]. Bagsvaerd, Denmark: Novo Nordisk A/S;2015.

Werner H, Chantelau EA, "Differences in Bioactivity Between Human Insulin and Insulin Analogues Approved for Therapeutic Use—Compilation of Reports from the Past 20 Years," Diabetol Metabol Syndrome 2011;3(13).

Yates RA, Nanney LB, Gates RE, et al. "Epidermal Growth Factor and Related Growth Factors," Int J Dermatol 1991;30,687-94.

\* cited by examiner

SEQUENCE LISTING

```
<160> NUMBER OF SEQ ID NOS: 4

<210> SEQ ID NO 1
<211> LENGTH: 53
<212> TYPE: PRT
<213> ORGANISM: Homo sapiens

<400> SEQUENCE: 1

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 2
<211> LENGTH: 54
<212> TYPE: PRT
<213> ORGANISM: Artificial Sequence
<220> FEATURE:
<223> OTHER INFORMATION: Synthetic peptide

<400> SEQUENCE: 2

Gly Asn Ser Asp Ser Glu Cys Pro Leu Ser His Asp Gly Tyr Cys Leu
1               5                   10                  15

His Asp Gly Val Cys Met Tyr Ile Glu Ala Leu Asp Lys Tyr Ala Cys
            20                  25                  30

Asn Cys Val Val Gly Tyr Ile Gly Glu Arg Cys Gln Tyr Arg Asp Leu
        35                  40                  45

Lys Trp Trp Glu Leu Arg
    50

<210> SEQ ID NO 3
<211> LENGTH: 54
<212> TYPE: PRT
<213> ORGANISM: Artificial Sequence
<220> FEATURE:
<223> OTHER INFORMATION: Synthetic peptide

<400> SEQUENCE: 3

Gly Asn Ser Asp Ser Glu Cys Pro Leu Ser His Asp Gly Tyr Cys Leu
1               5                   10                  15

His Asp Gly Val Cys Met Tyr Ile Glu Ala Leu Asp Arg Tyr Ala Cys
            20                  25                  30

Asn Cys Val Val Gly Tyr Ile Gly Glu Arg Cys Gln Tyr Arg Asp Leu
        35                  40                  45

Arg Trp Trp Glu Leu Arg
    50

<210> SEQ ID NO 4
<211> LENGTH: 49
<212> TYPE: PRT
<213> ORGANISM: Artificial Sequence
<220> FEATURE:
```

<223> OTHER INFORMATION: Synthetic peptide

<400> SEQUENCE: 4

```
Gly Asn Ser Asp Ser Glu Cys Pro Leu Ser His Asp Gly Tyr Cys Leu
1               5                   10                  15

His Asp Gly Val Cys Met Tyr Ile Glu Ala Leu Asp Lys Tyr Ala Cys
            20                  25                  30

Asn Cys Val Val Gly Tyr Ile Gly Glu Arg Cys Gln Tyr Arg Asp Leu
        35                  40                  45

Lys
```

FATTY ACID MODIFIED HUMAN EPIDERMAL GROWTH FACTOR

This application is a national phase application under 35 U.S.C. § 371 of International Application No. PCT/US2018/043598, filed Jul. 25, 2018, which claims the benefit of U.S. Provisional Application No. 62/537,808, filed on Jul. 27, 2017, the entire contents of each of which are hereby incorporated by reference.

STATEMENT REGARDING FEDERALLY SPONSORED RESEARCH OR DEVELOPMENT

This invention was made with government support under grant no. UL1 TR000448 awarded by the National Institutes of Health (NIH)/National Center for Advancing Translational Sciences (NCATS). The government has certain rights in the invention.

BACKGROUND

I. Field

This disclosure relates generally to the fields of medicine, protein biology and biochemistry. More particularly, it relates to the development of novel EGF molecules having fatty acids conjugated thereto.

II. Related Art

Short gut syndrome (SGS) results from the surgical removal of a significant length of small intestine (usually defined as one-half the total length or more) due to necrosis, loss of tissue integrity and function, or gut perforation. In the pediatric population, the most common cause of SGS is necrotizing enterocolitis (NEC). SGS has a mortality rate of approximately 25%, making it one of the most lethal conditions for infants and children. An estimated 20,000 children in the United States alone have SGS. There is currently no cure for SGS. It is an orphan disease for which there is only one surgical cure, small bowel transplant, which is necessary in about 25% of children with SGS. The current 5-year survival rate for small bowel transplant is 50% (Garg, 2011; LaRosa 2011). SGS survivors or those patients whose remaining small intestine adapts by increasing intestinal surface area, will still depend on parenteral nutritional (PN) support, as they are unable to absorb nutrients, electrolytes, and fluids normally. SGS patients can require up to 7 nights of PN per week for up to 22 hours a session (Short Bowel Syndrome Foundation; www.shortbowelfoundation.org/). SGS patients receiving PN still suffer from severe diarrhea, often accompanied by dehydration, malnutrition, weight loss and fatigue. PN treatment typically costs over $200,000 per year. There are currently two daily-dosed subcutaneous therapeutic agents approved for improving the efficiency of parenteral support in SBS patients, but not approved to treat the underlying pathology: Zorbtive® (recombinant human growth hormone), and Gattex® (recombinant human glucagon-like peptide 2). The one-year cost of treatment with Zorbtive® or Gattex® is approximately $300,000, not including nutrition and hospital costs (Matthew, 2013). Neither drug is approved for use in children.

Human epidermal growth factor (hEGF) has shown promise as a treatment for SGS by improving small bowel adaptation after SBR. Indeed, clinical trials of hEGF in pediatric patients with SGS have shown hEGF to be well tolerated intravenously for a 6-day trial, and orally in a 6-week trial (Sigalet, 2005; Sullivan 2007). These studies, although small, also showed significant increases in mucosal thickness, crypt surface area, carbohydrate absorption, and tolerance of enteral feeding.

Based on this evidence, there is great therapeutic potential for hEGF that has been modified to have an extended intravenous half-life for the treatment of SGS. hEGF that possesses an extended half-life in the bloodstream would require lower and less frequent doses, as well as a more sustained, controlled dose of hEGF that would be far superior to unmodified hEGF. Such a treatment would increase the patient's ability to absorb nutrients and decrease the length as well as the cost of PN treatment. However, clinical application of this approach is limited due to the very short half-life of hEGF (~2 minutes) in vivo.

SUMMARY

In accordance with the present disclosure, there is provided 1 modified epidermal growth factor (EGF) molecules of the formula:

$$X-(Y)_m-Z \qquad (I)$$

wherein:
Z represents an EGF recombinant protein;
X represents a fatty acid;
Y represents a linker element between X and the N-terminus of EGF; and
m=0-8,
or a pharmaceutically acceptable salt thereof.

In some embodiments, Z represents a modified epidermal growth factor (EGF) protein selected from:
Native human EGF wherein Lys28 is mutated to another amino acid, such as Arg,
Native human EGF wherein Lys28 is mutated to Arg and Lys48 is mutated to another amino acid, such as Arg,
Native human EGF is truncated, such as after residue Lys48,
Native human EGF is truncated after residue Lys48, wherein Lys28 is mutated to Arg,
Native human EGF is truncated after residue Lys48, wherein Lys28 is mutated to Arg and Lys48 is mutated to Arg,
Gly-EGF wherein Lys28 is mutated to another amino acid, such as Arg,
Gly-EGF wherein Lys28 is mutated to Arg and Lys48 is mutated to another amino acid, such as Arg,
Gly-EGF is truncated, such as after residue Lys48,
Gly-EGF is truncated after residue Lys48, wherein Lys28 is mutated to Arg,
Gly-EGF is truncated after residue Lys48, wherein Lys28 is mutated to Arg and Lys48 is mutated to Arg,
Ser-EGF wherein Lys28 is mutated to another amino acid, such as Arg,
Ser-EGF wherein Lys28 is mutated to Arg and Lys48 is mutated to another amino acid, such as Arg,
Ser-EGF is truncated, such as after residue Lys48,
Ser-EGF is truncated after residue Lys48, wherein Lys28 is mutated to Arg, or
Ser-EGF is truncated after residue Lys48, wherein Lys28 is mutated to Arg and Lys48 is mutated to Arg;
or a pharmaceutically acceptable salt thereof. In some embodiments, EGF is selected from:

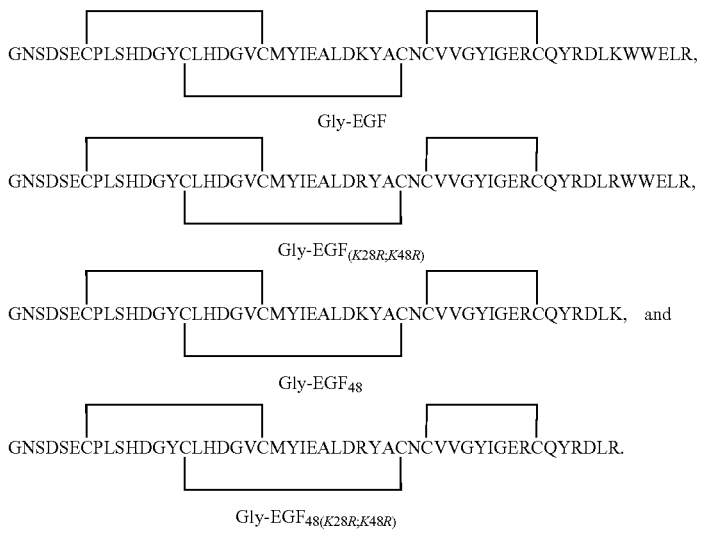

In some embodiments, X is —C(O)R$_a$, wherein R$_a$ is alkyl$_{(C6-C24)}$, alkenyl$_{(C6-C24)}$, or a substituted version of both groups. X may be

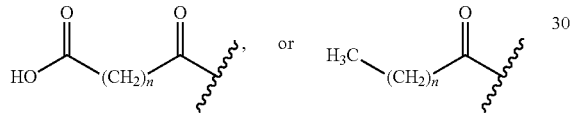

wherein n=12, 14, 16, 18, or 20;
or a pharmaceutically acceptable salt thereof.

In some embodiments, Y is a linker element comprising a first linking group and a spacer. In some embodiments, the spacer is a covalent bond, a PEG group, an alkanediyl$_{(C1-C12)}$, a substituted alkanediyl$_{(C1-C12)}$, an alkenediyl$_{(C1-C12)}$, a substituted alkenediyl$_{(C1-C12)}$, an alkoxydiyl$_{(C1-C12)}$, or a substituted alkoxydiyl$_{(C1-C12)}$. In some embodiments, Y is selected from one or more α-amino acids, β-amino acids, γ-amino acids,

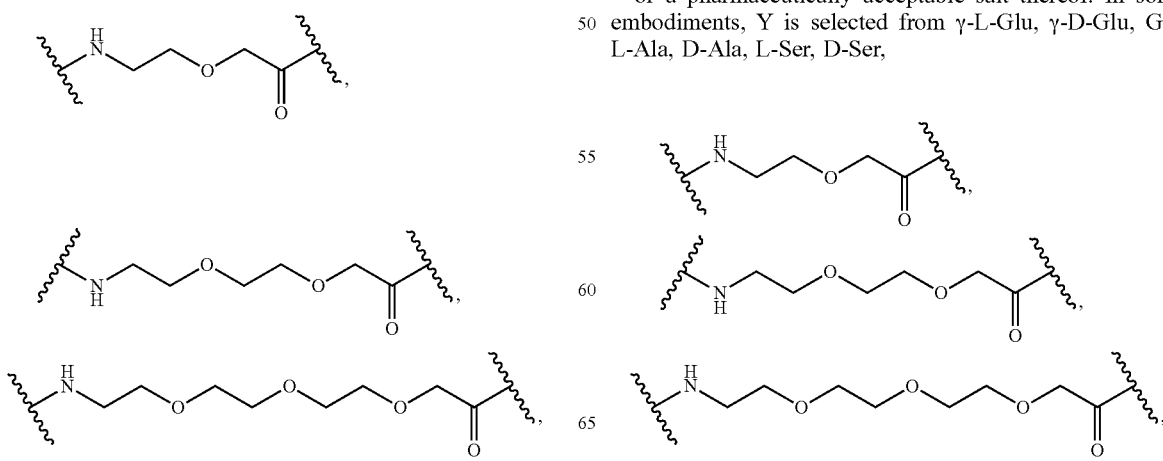

or a pharmaceutically acceptable salt thereof. In some embodiments, Y is selected from γ-L-Glu, γ-D-Glu, Gly, L-Ala, D-Ala, L-Ser, D-Ser,

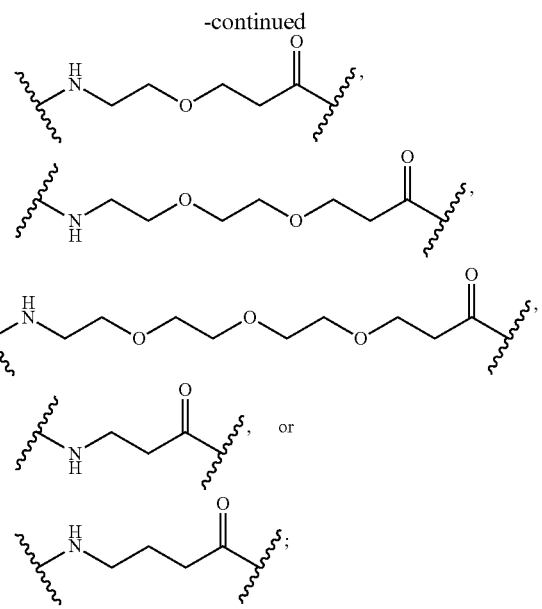

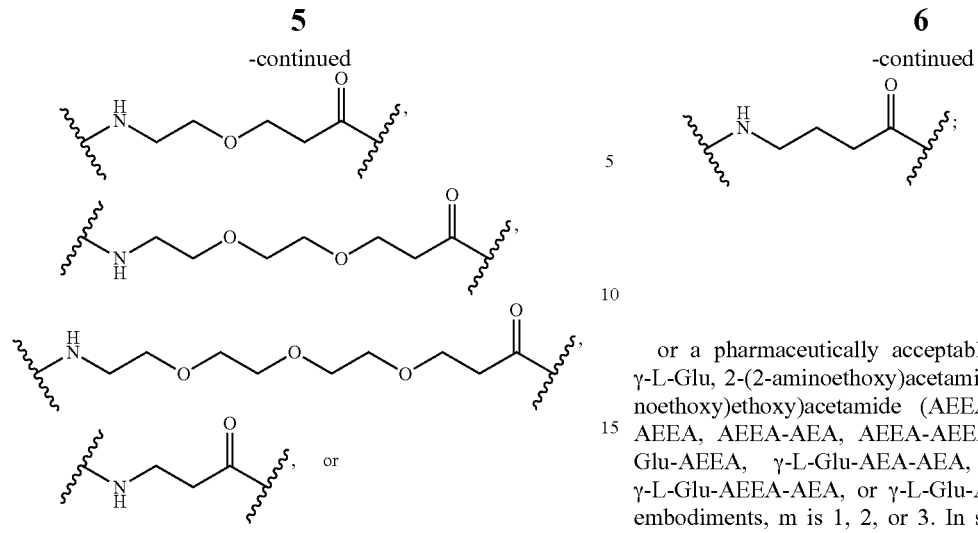
or a pharmaceutically acceptable salt thereof such as γ-L-Glu, 2-(2-aminoethoxy)acetamide (AEA), 2-(2-(2-aminoethoxy)ethoxy)acetamide (AEEA), AEA-AEA, AEA-AEEA, AEEA-AEA, AEEA-AEEA, γ-L-Glu-AEA, γ-L-Glu-AEEA, γ-L-Glu-AEA-AEA, γ-L-Glu-AEA-AEEA, γ-L-Glu-AEEA-AEA, or γ-L-Glu-AEEA-AEEA. In some embodiments, m is 1, 2, or 3. In some embodiments, the molecules are further defined as:
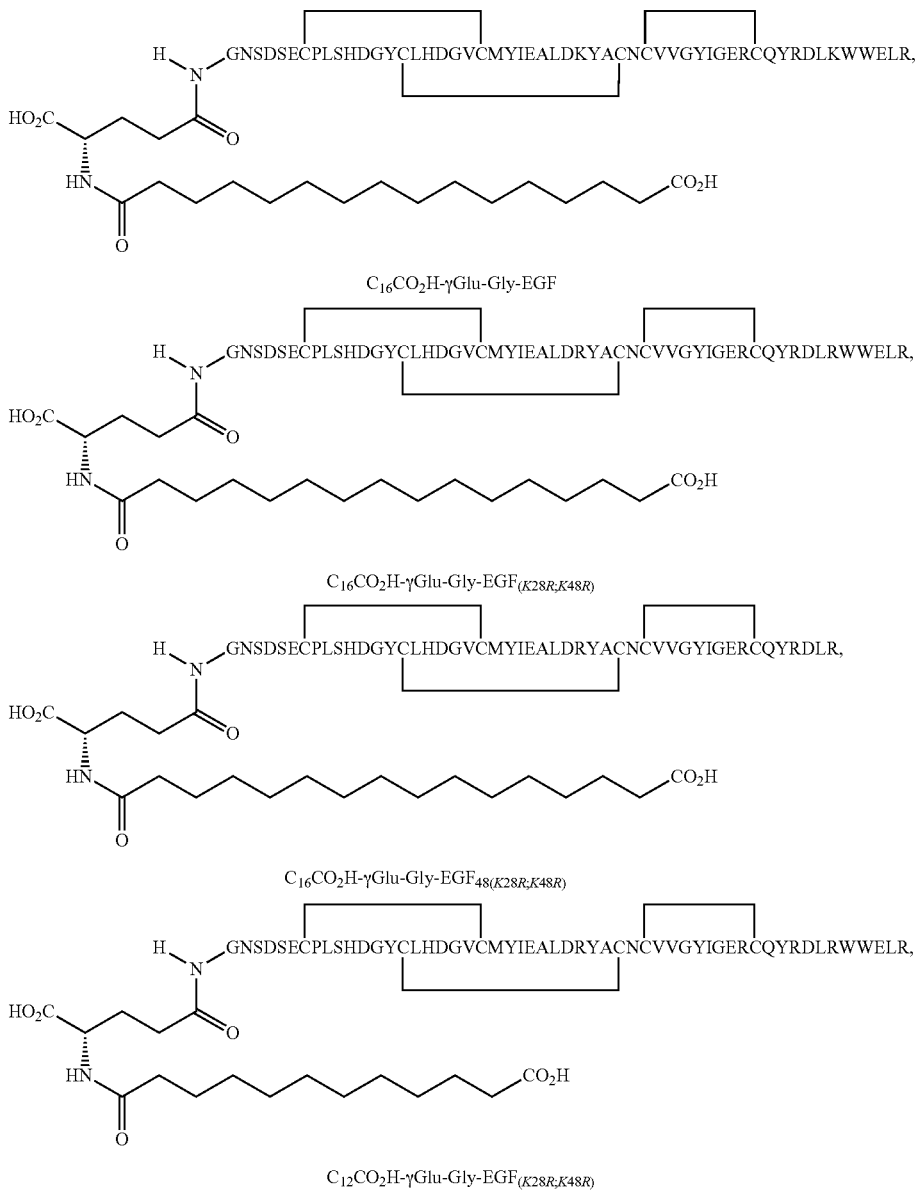

-continued
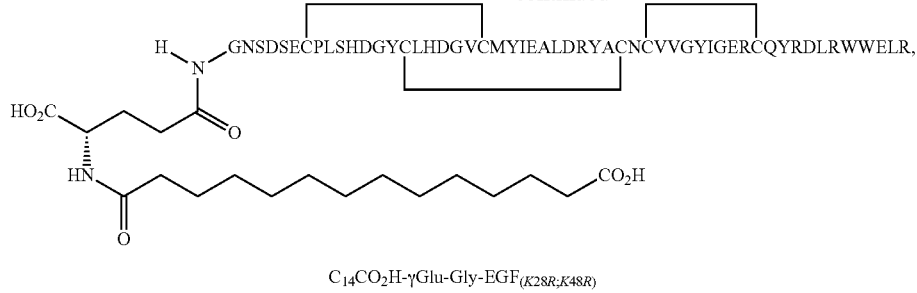
C₁₄CO₂H-γGlu-Gly-EGF₍K28R;K48R₎
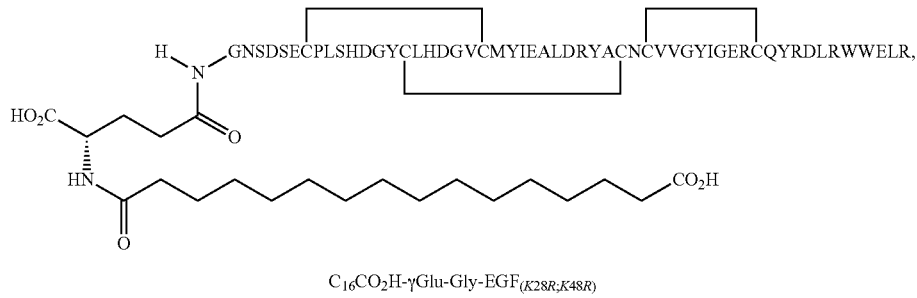
C₁₆CO₂H-γGlu-Gly-EGF₍K28R;K48R₎
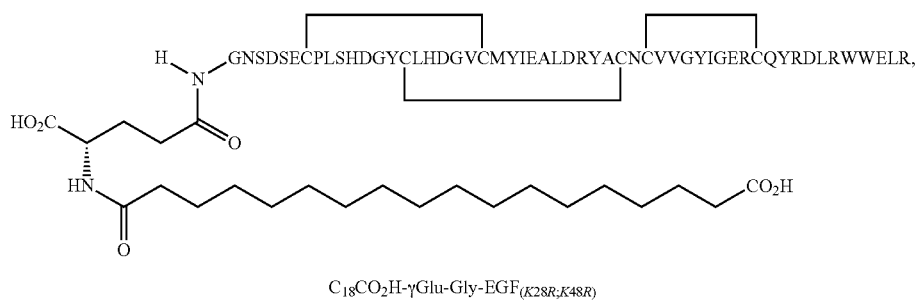
C₁₈CO₂H-γGlu-Gly-EGF₍K28R;K48R₎
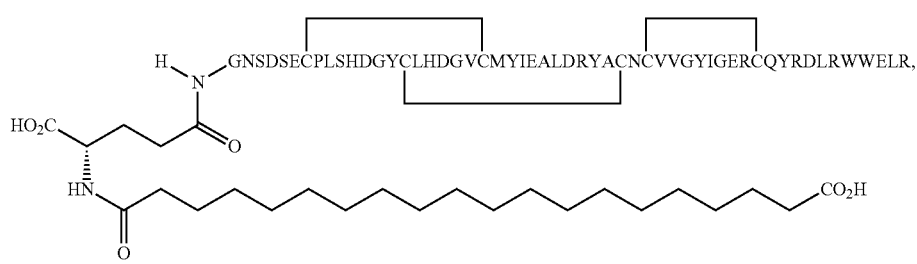
C₂₀CO₂H-γGlu-Gly-EGF₍K28R;K48R₎
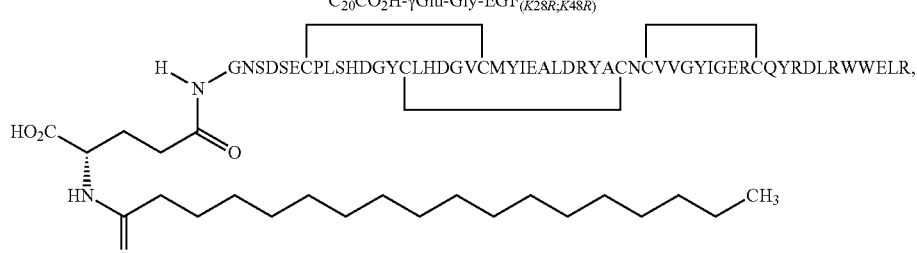
C₁₈CH₃-γGlu-Gly-EGF₍K28R;K48R₎

-continued
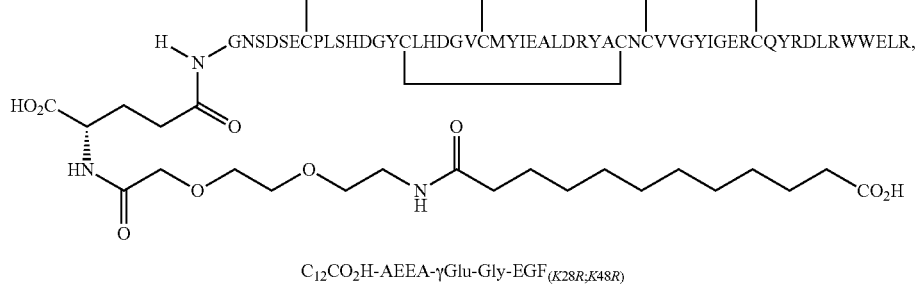
$C_{12}CO_2H$-AEEA-γGlu-Gly-EGF$_{(K28R;K48R)}$
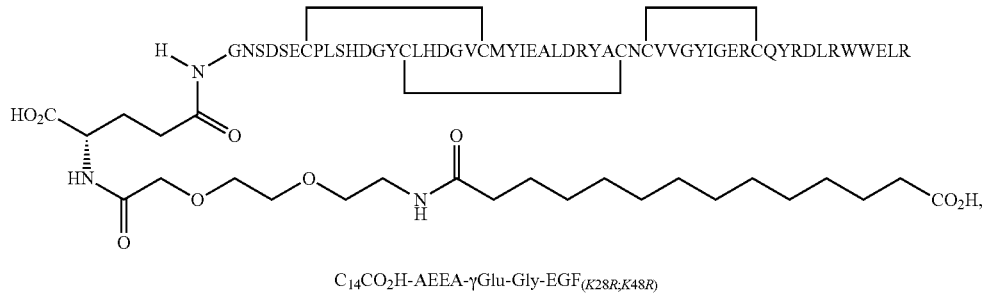
$C_{14}CO_2H$-AEEA-γGlu-Gly-EGF$_{(K28R;K48R)}$
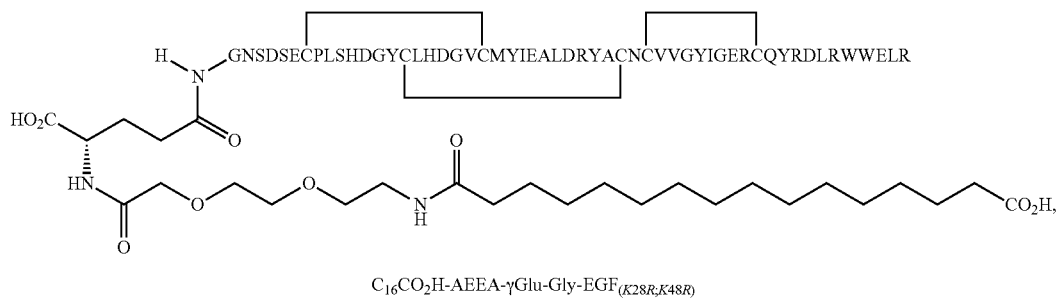
$C_{16}CO_2H$-AEEA-γGlu-Gly-EGF$_{(K28R;K48R)}$
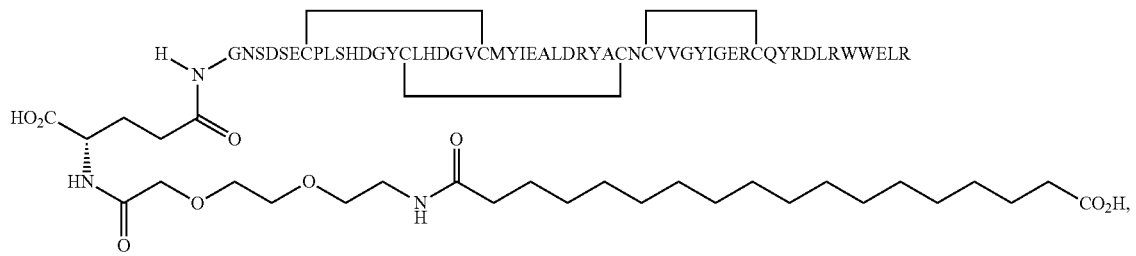
$C_{18}CO_2H$-AEEA-γGlu-Gly-EGF$_{(K28R;K48R)}$
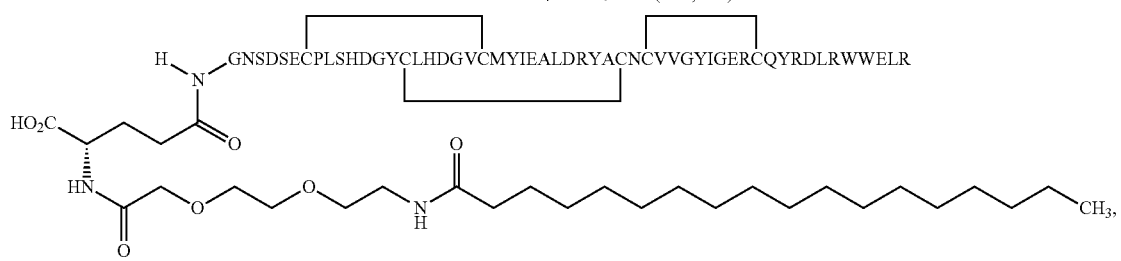
$C_{18}CH_3$-AEEA-γGlu-Gly-EGF$_{(K28R;K48R)}$

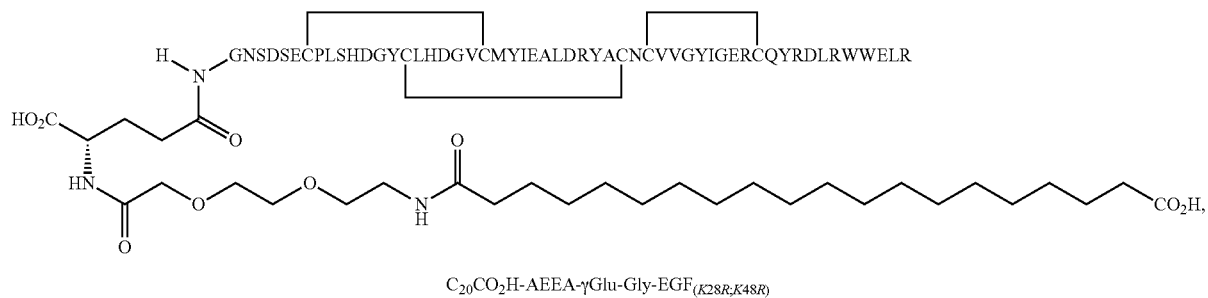
C$_{20}$CO$_2$H-AEEA-γGlu-Gly-EGF$_{(K28R;K48R)}$
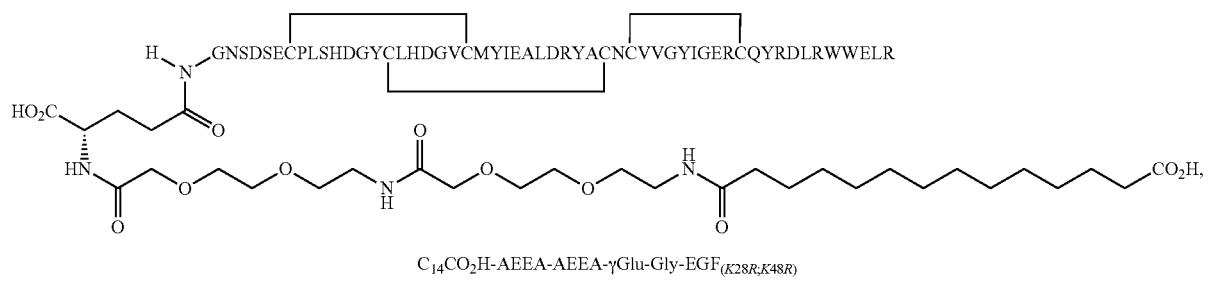
C$_{14}$CO$_2$H-AEEA-AEEA-γGlu-Gly-EGF$_{(K28R;K48R)}$
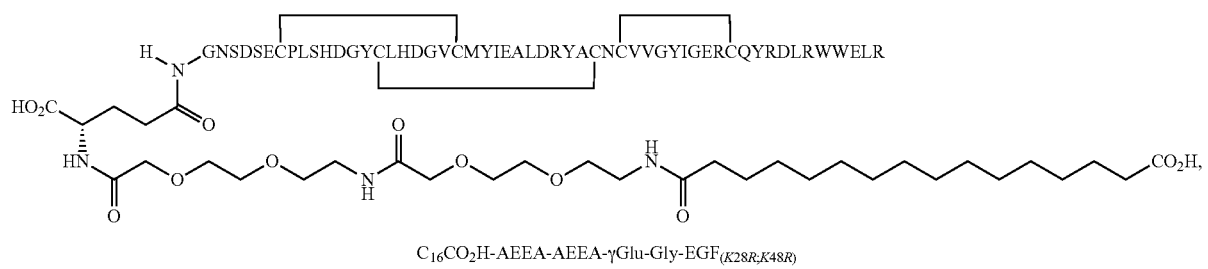
C$_{16}$CO$_2$H-AEEA-AEEA-γGlu-Gly-EGF$_{(K28R;K48R)}$
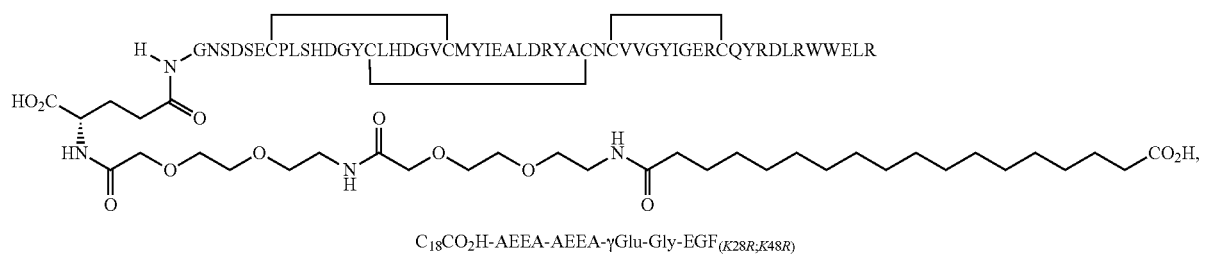
C$_{18}$CO$_2$H-AEEA-AEEA-γGlu-Gly-EGF$_{(K28R;K48R)}$
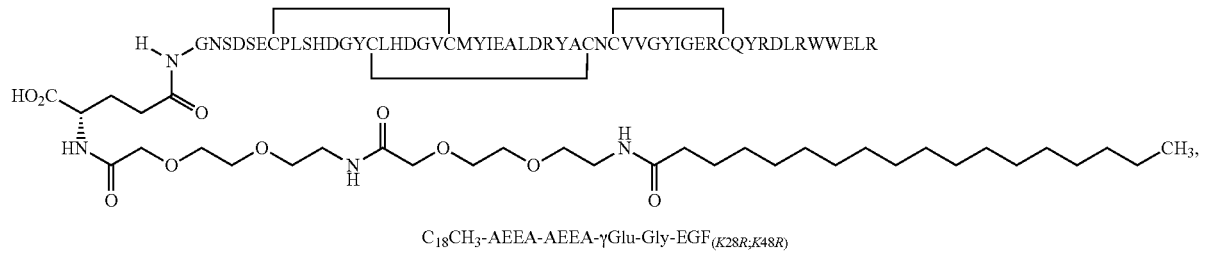
C$_{18}$CH$_3$-AEEA-AEEA-γGlu-Gly-EGF$_{(K28R;K48R)}$
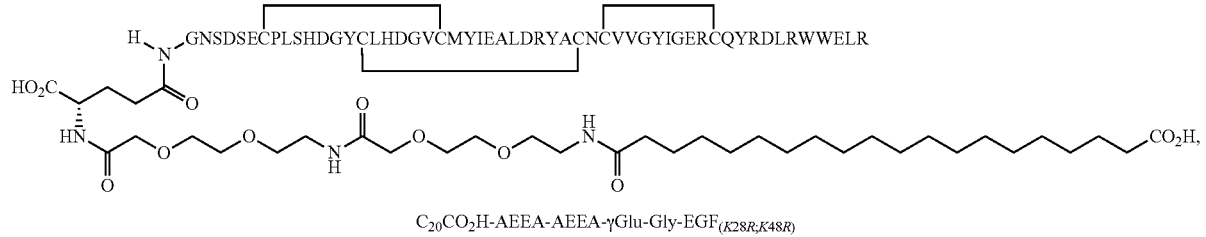
C$_{20}$CO$_2$H-AEEA-AEEA-γGlu-Gly-EGF$_{(K28R;K48R)}$ -continued

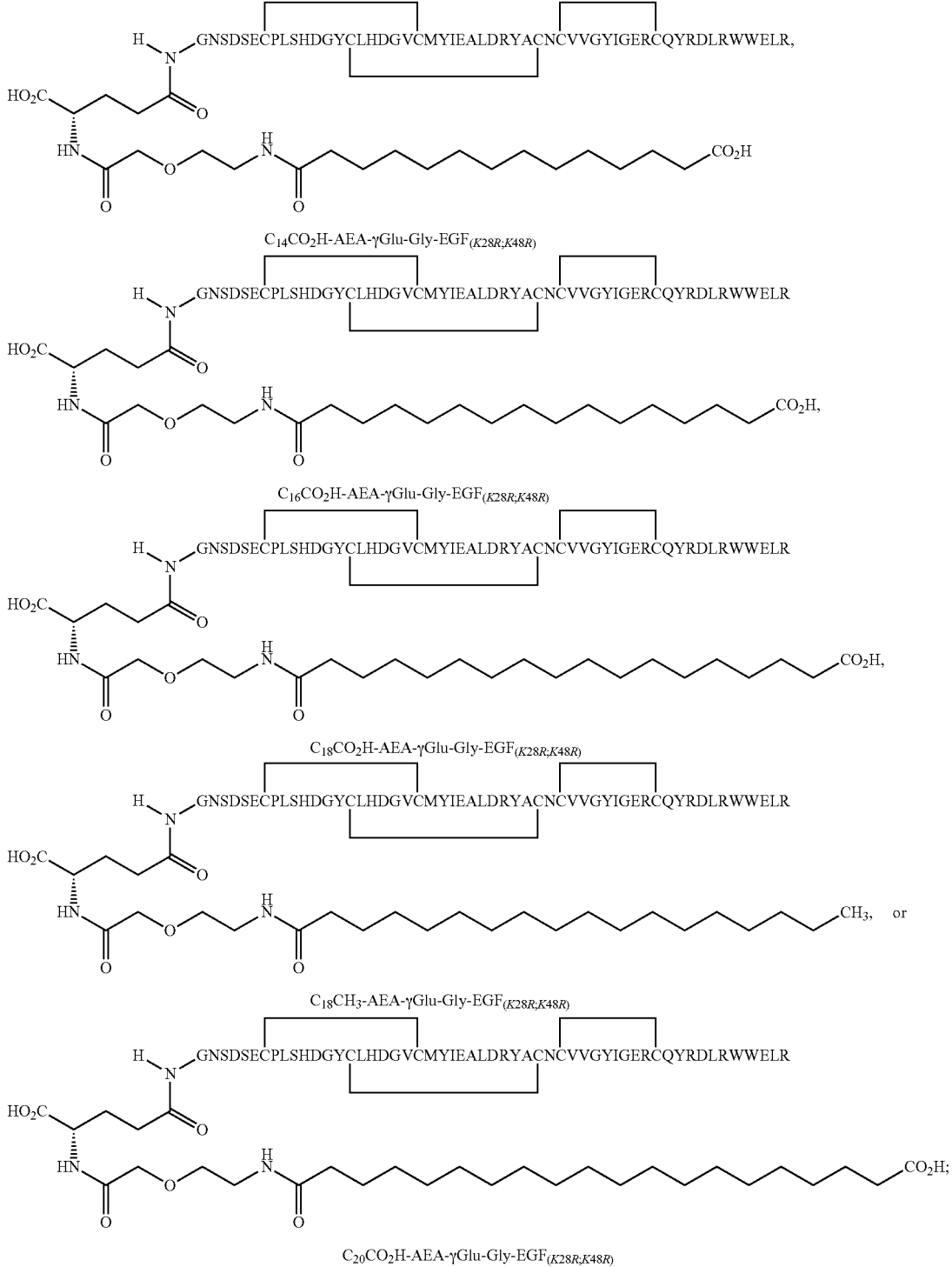

or a pharmaceutically acceptable salt thereof.

In yet another aspect, the present disclosure provides pharmaceutical composition comprising:

(A) a EGF molecule described herein; and
(B) an excipient.

In some embodiments, the pharmaceutical composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in crémes, in lipid compositions, via a catheter, via a lavage, via continuous infusion, via infusion, via inhalation, via injection, via local delivery, or via localized perfusion. In some embodiments, the pharmaceutical composition is formulated for oral administration, intraarterial administration, intraperitoneal administration, intravenous administration, topical, or subcutaneous administration. In some embodiments, the pharmaceutical composition is formulated for administration via intravenous infusion. In some embodiments, the pharmaceutical composition comprises a unit dose form of the EGF molecule in the range of 0.01 to 5 mg.

In still yet another aspect, the present disclosure provides method sof treating short bowel syndrome (SBS) comprising administered an EGF molecule or pharmaceutical composition described herein to a subject in need thereof. In some embodiments, said EGF molecule is administered orally, intraarterially, intraperitoneally, intravenously, or subcutaneously. In some embodiments, said EGF molecule is administered more than once. In some embodiments, said EGF molecule is administered daily, every other day, every third day, twice a week, weekly, every two weeks or monthly. In some embodiments, said EGF molecule is administered at a dose of 0.01 to 5 mg.

In some embodiments, said SBS is caused by Crohn's disease, volvulus, a tumor, injury, necrotizing enterocolitis, bypass surgery to treat obesity, or surgery to remove otherwise diseased or damaged portions of the small intestine. In some embodiments, said subject has less than 10 feet of small intestine, less than 7 feet of small intestine, or has less than 5 feet of small intestine. In some embodiments, the methods further comprise administering to said subject a second SBS therapy. In some embodiments, said second SBS therapy is one of more of anti-diarrheal medicine, vitamin, mineral supplements and L-glutamine powder mixed with water, $H_2$ blocker and proton pump inhibitors to reduce stomach acid, antibiotics, or lactase supplement. In some embodiments, said administration improves one or more symptoms of SBS, such as abdominal pain, diarrhea and steatorrhea, fluid depletion, weight loss and malnutrition, fatigue, malabsorption of vitamins and/or minerals, anemia, hyperkeratosis (scaling of the skin), easy bruising, muscle spasms, poor blood clotting, and bone pain.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C≤8)}$" or the class "alkene$_{(C≤8)}$" is two. Compare with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. When any of the chemical groups or compound classes defined herein is modified by the term "substituted", any carbon atom(s) in the moiety replacing a hydrogen atom is not counted. Thus methoxyhexyl, which has a total of seven carbon atoms, is an example of a substituted alkyl$_{(c1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group refers to a planar unsaturated ring of atoms with 4n+2 electrons in a fully conjugated cyclic π system.

The term "alkyl" when used without the "substituted" modifier refers to a monovalent saturated aliphatic group with a carbon atom as the point of attachment, a linear or branched acyclic structure, and no atoms other than carbon and hydrogen. The groups —$CH_3$ (Me), —$CH_2CH_3$ (Et), —$CH_2CH_2CH_3$ (n-Pr or propyl), —$CH(CH_3)_2$ (i-Pr, $^i$Pr or isopropyl), —$CH_2CH_2CH_2CH_3$ (n-Bu), —$CH(CH_3)CH_2CH_3$ (sec-butyl), —$CH_2CH(CH_3)_2$ (isobutyl), —$C(CH_3)_3$ (tert-butyl, t-butyl, t-Bu or $^t$Bu), and —$CH_2C(CH_3)_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —$CH_2$— (methylene), —$CH_2CH_2$—, —$CH_2C(CH_3)_2CH_2$—, and —$CH_2CH_2CH_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =$CH_2$, =$CH(CH_2CH_3)$, and =$C(CH_3)_2$. An "alkane" refers to the class of compounds having the formula H—R, wherein R is alkyl as this term is defined above. When any of these terms is used with the "substituted" modifier one or more hydrogen atom has been independently replaced by —OH, —F, —Cl, —Br, A, —$NH_2$, —$NO_2$, —$CO_2H$, —$CO_2CH_3$, —CN, —SH, —$OCH_3$, —$OCH_2CH_3$, —$C(O)CH_3$, —$NHCH_3$, —$NHCH_2CH_3$, —$N(CH_3)_2$, —$C(O)NH_2$, —$C(O)NHCH_3$, —$C(O)N(CH_3)_2$, —$OC(O)CH_3$, —$NHC(O)CH_3$, —$S(O)_2OH$, or —$S(O)_2NH_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "alkenyl" when used without the "substituted" modifier refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$0H, or —S(O)$_2$NH$_2$. The groups —CH=CHF, —CH=CHCl and —CH=CHBr are non-limiting examples of substituted alkenyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), or —OC(CH$_3$)$_3$ (tert-butoxy). The term "alkenyloxy" when used without the "substituted" modifier, refers to groups, defined as —OR, in which R is alkenyl. The term "alkoxydiyl" when used without the "substituted" modifier refers to a divalent unsaturated aliphatic group, with two carbon atoms as points of attachment, a linear or branched, a linear or branched acyclic structure, and contains at least one or more oxygen atom within the linear or branched structure. The groups —CH$_2$OCH$_2$—, —CH$_2$OCH(CH$_3$)CH$_2$—, and —CH$_2$OCH$_2$CH$_2$OCH$_2$— are non-limiting examples of alkoxydiyl groups. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating or preventing a disease, is an amount sufficient to effect such treatment or prevention of the disease.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

As used herein, the term "patient" or "subject" refers to a living mammalian organism, such as a human, monkey, cow, horse, sheep, goat, dog, cat, mouse, rat, guinea pig, or transgenic species thereof. In certain embodiments, the patient or subject is a primate. Non-limiting examples of human patients are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Non-limiting examples of such salts include acid addition salts formed with inorganic acids such as hydrochloric acid, hydrobromic acid, sulfuric acid, nitric acid, and phosphoric acid; or with organic acids such as 1,2-ethanedisulfonic acid, 2-hydroxyethanesulfonic acid, 2-naphthalenesulfonic acid, 3-phenylpropionic acid, 4,4'- methylenebis(3-hydroxy-2-ene-1-carboxylic acid), 4-methylbicyclo [2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, and trimethylacetic acid. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Non-limiting examples of acceptable organic bases include ethanolamine, diethanolamine, triethanolamine, tromethamine, and N-methylglucamine. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

A "pharmaceutical drug" (also referred to as a pharmaceutical, pharmaceutical agent, pharmaceutical preparation, pharmaceutical composition, pharmaceutical formulation, pharmaceutical product, medicinal product, medicine, medication, medicament, or simply a drug) is a drug used to diagnose, cure, treat, or prevent disease. An active ingredient (AI) (defined above) is the ingredient in a pharmaceutical drug or a pesticide that is biologically active. The similar terms active pharmaceutical ingredient (API) and bulk active are also used in medicine, and the term active substance may be used for pesticide formulations. Some medications and pesticide products may contain more than one active ingredient. In contrast with the active ingredients, the inactive ingredients are usually called excipients (defined above) in pharmaceutical contexts.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

It is contemplated that any embodiment discussed in this specification can be implemented with respect to any method or composition of the disclosure, and vice versa. Furthermore, compositions and kits of the disclosure can be used to achieve methods of the disclosure.

Throughout this application, the term "about" is used to indicate that a value includes the inherent variation of error for the device, the method being employed to determine the value, or the variation that exists among the study subjects.

BRIEF DESCRIPTION OF THE DRAWINGS

So that the manner in which the above-recited features, aspects and advantages of the disclosure, as well as others that will become apparent, are attained and can be understood in detail, more particular description of the disclosure briefly summarized above can be had by reference to the embodiments thereof that are illustrated in the drawings that form a part of this specification. It is to be noted, however, that the appended drawings illustrate some embodiments of the disclosure and are, therefore, not to be considered limiting of the disclosure's scope, for the disclosure can admit to other equally effective embodiments.

DETAILED DESCRIPTION OF THE DISCLOSURE

Figure 1:
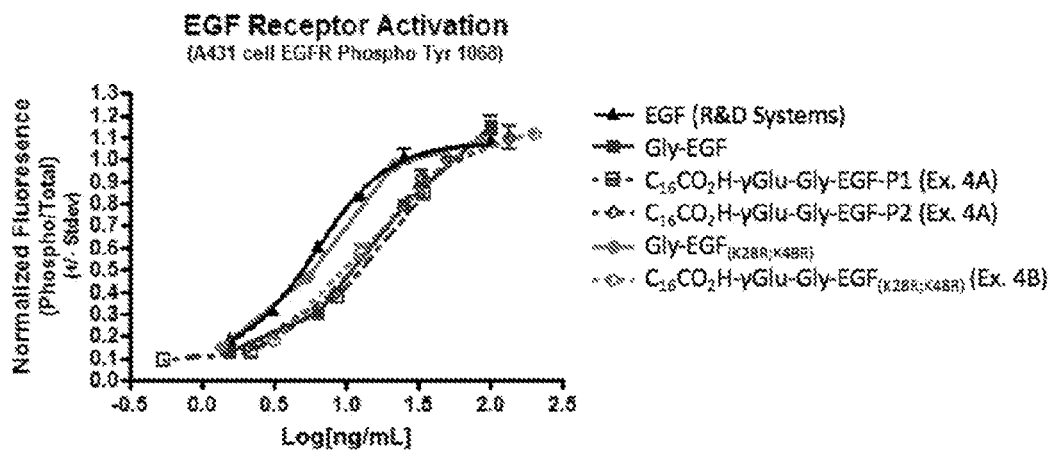
FIG. 1—Activation of EGFR by EGF variants and their corresponding fatty acid conjugates.

As discussed above, EGF shows great promise in the treatment of short gut syndrome (SGS), but is hampered by its short half-life in vivo. The inventors proposed that a strategic modification of EGF to increase its stability and duration of action could produce a viable therapeutic for SGS.

To this end, the inventors sought to stabilize hEGF through enhanced serum albumin association, which has been shown to be safe and effective at dramatically extending the half-life of similarly sized therapeutic proteins in humans such as insulin and GLP-1. The inventors hypothesized that strategic modification of the hEGF protein with a fatty acid conjugate will increase its half-life and duration of action in vivo, thus providing a more practical and cost-efficient therapy than native hEGF to treat patients with SGS, improving ability to absorb nutrients and ultimately reducing infant mortality.

The inventors proceeded to have designed and synthesized fatty acid (FA) conjugates of epidermal growth factor (EGF) and of an EGF mutant. They have demonstrated that these FA-EGF conjugates activate the EGF receptor (EGFR) in vitro with potencies similar to native EGF. They have demonstrated that these FA-EGF conjugates persist longer than non-FA conjugated EGF proteins when dosed intravenously in mice. Based on literature precedent for other FA-conjugates of small proteins, the inventors expect that these FA-EGF conjugates with have dramatically longer half-lives than native EGF in vivo. Thus, FA-EGF conjugates have the potential to be developed as drugs for the treatment of short gut syndrome (SGS) and in the prevention of necrotizing enterocolitis (NEC).

These and other aspects of the disclosure are set forth in detail below.

I. EPIDERMAL GROWTH FACTOR PREPARATIONS

Epidermal growth factor (EGF) stimulates cell growth and differentiation by binding to its receptor, EGFR. EGF was originally described as a secreted peptide found in the submaxillary glands of mice and in human urine. EGF has since been found in many human tissues including submandibular gland, parotid gland. Initially, human EGF was known as urogastrone.

Salivary EGF, which seems also regulated by dietary inorganic iodine, also plays an important physiological role in the maintenance of oro-esophageal and gastric tissue integrity. The biological effects of salivary EGF include healing of oral and gastroesophageal ulcers, inhibition of gastric acid secretion, stimulation of DNA synthesis as well as mucosal protection from intraluminal injurious factors such as gastric acid, bile acids, pepsin, and trypsin and to physical, chemical and bacterial agents.

hEGF is a 6 kD protein made of 53 amino acids (NSD-SECPLSHDGYCLHDGVCMYIEALDKY-ACNCVVGYIGERCQYRDLKWWELR (SEQ ID NO: 1)) produced in the salivary glands and found in platelets, saliva, breast milk and plasma. The binding of EGF to its receptor, EGFR, induces autophosphorylation of tyrosine 1068 in the cytosolic tyrosine kinase domain of the receptor, which begins a signaling cascade that induces proliferation and differentiation of epithelial cells in the gastrointestinal tract. EGFR is primarily expressed on the serosal side (blood vessel side) of cells lining the GI tract (Playford e al., 1996). EGF has been shown to have greater efficacy through a systemic dosing route versus the oral route in rat models (Playford et al., 1996). EGF administration after small bowel resection in rats was shown to promote an adaptation to shortened bowel length by increasing DNA, mRNA, protein synthesis, villus crypt height and depth, animal body weight, intestinal weight, and bowel length (Chaet et al., 1994). Warner and coworkers found that mice that underwent SBR had a two-fold increase of EGFR expression in crypts compared to sham animals. Proliferation in the crypt area was most affected and supports the hypothesis that EGFR signaling is involved in the mitogenic stimulus of adaptation (McMellen et al., 2010). It was found that administration of EGF was effective for enhancing adaptation if given immediately after SBR, but not if adaptation had reached a plateau. Warner postulates that delay in the initiation of EGF treatment may account for the modest clinical outcomes using other growth factors in other reports. Warner also found that removing the salivary glands of mice, a major source of endogenous EGF, and attenuated increase in ileal crypt height usually observed after SBR. EGF replacement therapy restored this increase. It has been hypothesized that EGF retards the rate of apoptosis in the intestine, increasing mucosal proliferation. Findings that EGF administration following SBR causes a decrease in the pro-apoptotic gene bax, and an increase in anti-apoptotic bcl-w, support this hypothesis (Stern et al., 2000; Sheng et al., 2007).

A. Fatty Acids for Conjugation to EGF Molecules

In some aspects, the EGF compounds of the present disclosure are linked with one or more fatty acids. A fatty acid is a medium or long chain aliphatic hydrocarbon with at least one terminal carboxylic acid group such as compounds of the formula $R_aC(O)OH$, wherein $R_a$ is an alkyl group, an alkenyl group, or a substituted version of either group. The medium chain aliphatic hydrocarbon is a 6-12 carbon atom alkyl group, alkenyl group, or a substituted version of either group. In other embodiments, the long chain aliphatic hydrocarbon is a 12-24 carbon atom alkyl group, alkenyl group, or a substituted version of either group. Some of the fatty acids may have a 6, 8, 10, 12, 14, 16, 18, 20, 22, or 24 carbon atoms.

In some embodiments, the fatty acid is substituted with one or more carboxylic acid groups. The fatty acid may be a dicarboxylic acid with a carboxylic acid at the terminal of each the aliphatic hydrocarbon group. The fatty acids may be joined to the EGF molecules through a peptide bond (e.g. through the formation of one or more amide bonds) or joined to a linker through a peptide bond. The linker may allow the conjugations of two or more fatty acids to the EGF molecule.

B. Variation in EGF Sequences

EGF has many residues conserved across rat, mouse, guinea pig and human species (Savage 1972, Carpenter 1979, Simpson 1985). In particular, six cysteine residues at positions 6, 14, 20, 31, 33, and 42 are conserved as they form three disulfide bridges to provide conserved tertiary protein structure. Also conserved across all four species are residues as positions 7, 9, 11, 12, 13, 15, 18, 21, 24, 29, 32, 34, 36, 37, 39, 41, 46, and 47. Many of these residues may be expected to facilitate or provide key binding interactions with the corresponding EGFR. It is also known that both the full length human EGF (53 residues) and a truncated form (48 residues), which results from trypsin cleavage, retain strong binding affinity and activation of the EGFR (Calnan 2000, Gregory 1998). Mutagenesis studies have been reported for various residues to correlate the effect of replacement of specific residues on binding of EGF to the EGFR or activation of the EGFR (Campion 1990, Engler 1992, Tadaki 1993). An x-ray crystal structure of EGF bound to EGFR has been solved which shows key binding interactions and also identifies residues not directly involved in binding (Ogiso 2002).

Analysis of the EGF-EGFR crystal structure and mutagenesis studies suggests that certain residues may be mutated without compromising, or may even enhance, the binding and activation of EGFR by EGF proteins. Indeed, the inventors have demonstrated herein that both Lys28 and Lys48 may be simultaneously replaced by Arg to produce an EGF derivative protein (Gly-EGF$_{(K28R;K48R)}$) that retains activity comparable to native human EGF. Other such changes can be envisioned upon detailed study of the crystal structure and mutagenesis reports. Such changes are useful in that they may alter physical properties, metabolic stability, and other characteristics of EGF proteins. In the example of Gly-EGF$_{(K28R;K48R)}$, the replacement of two Lys residues with Arg greatly simplifies the synthesis of N-terminal specific fatty acid conjugates as the only primary amine available for reaction with the fatty acid acylation agent in the N-terminal glycine residue.

Therefore, the EGF compounds may comprise one or more conservative mutations at a position in either the full version or truncated version at any position other than the commonly conserved residues described above. The conserved residues which may not be modified include amino acids at positions 6, 7, 9, 11, 12, 13, 14, 15, 18, 20, 21, 24, 29, 31, 32, 33, 34, 36, 37, 39, 41, 42, 46, and 47. The EGF compounds may comprise 1, 2, 3, 4, or 5 conservative mutations at a position other than the commonly conserved residues described above.

C. Linkers

In some aspects, the EGF compounds is linked to the fatty acid through a linker. A linker is a group containing a first linking group and a spacer. The linker may optionally contain a second linking group. The first linking group and the second linking group are a functional group which reacts with another molecule to form a covalent bond. Some non-limiting examples of linking groups include an amine group, a carboxylic acid group, an azide group, an alkyne, an alkene, or a thiol reactive groups such as a maleimide or an iodoacetamide. In some embodiments, one of the first and the second linking groups are capable of joining a carboxylic acid of the fatty acid to the linker. The other linking group may be a group which is reactive with a functional group present on the EGF sequence such as a cysteine, an amine group from the N-terminus or the side chain of a lysine or arginine, or a carboxylic acid from the C-terminus or the side chain or a glutamic acid or aspartic acid.

In some aspects, the spacer group contains a covalent bond, an alkanediyl group, an alkenediyl group, an alkoxydiyl group, a PEG group or a substituted version of any of these groups. In some embodiments, these groups contain from a single carbon atom to 12 carbon atoms. In some embodiments, these groups may be substituted with one or more alkyl or cycloalkyl groups off the primary chain. In other embodiments, the PEG group may have from 1 to 20 repeating units. In still other embodiments, the PEG group is measured by its molecular weight as determined by GPC (gel permeability chromatography) and is from 100 to 10,000 Daltons. Additionally, the PEG group may be further derivatized to contain one or more branching PEG groups. These PEG groups may be terminated with another linking group or may contain a terminating group such as a hydrogen atom or a C1-C6 alkyl or substituted alkyl group.

D. Purification

In certain embodiments, the EGF reagents of the present invention may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In generating an EGF reagent of the present invention, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE. It will therefore be appreciated that under differing electrophoresis conditions, the apparent molecular weights of purified or partially purified expression products may vary.

II. THERAPY USING MODIFIED EGFS

A. Short Bowel Syndrome

Short bowel syndrome (SBS, or simply short gut) is a malabsorption disorder caused by a lack of functional small intestine. The primary symptom is diarrhea, which can result in dehydration, malnutrition, and weight loss. Other symptoms may include bloating, heartburn, feeling tired, lactose intolerance, and foul smelling stool. Complications can include anemia and kidney stones.

Most cases are due to the surgical removal of a large portion of the small intestine. This is most often required due to Crohn's disease in adults and necrotising enterocolitis in young children. Other causes include damage to the small intestine from other means and being born with an abnormally short intestine. It usually does not develop until less than 2 m (6.6 ft) of the normally 6.1 m (20 ft) small intestine remains.

Treatment may include a specific diet, medications, or surgery. The diet may include slightly salty and slightly sweet liquids, vitamin and mineral supplements, small frequent meals, and the avoidance of high fat food. Occasionally nutrients need to be given through an intravenous line, known as parenteral nutrition. Medications used may include antibiotics, antacids, loperamide, teduglutide, and growth hormone. Different types of surgery, including an intestinal transplant, may help some people.

Short bowel syndrome newly occurs in about three per million people each year. There are estimated to be about 15,000 people with the condition in the United States. Outcomes depend on the amount of bowel remaining and whether or not the small bowel remains connected with the large bowel. Intestinal failure is decreased intestinal function such that nutrients, water, and electrolytes are not sufficiently absorbed. Short bowel syndrome is when there is less than 2 m (6.6 ft) of working bowel and is the most common cause of intestinal failure.

The symptoms of short bowel syndrome can include abdominal pain, diarrhea and steatorrhea, fluid depletion, weight loss and malnutrition, and fatigue. Persons with short bowel syndrome may have complications caused by malabsorption of vitamins and minerals, such as deficiencies in vitamins A, D, E, K, $B_9$ (folic acid), and $B_{12}$, calcium, magnesium, iron, and zinc. These may appear as anemia, hyperkeratosis (scaling of the skin), easy bruising, muscle spasms, poor blood clotting, and bone pain.

Short bowel syndrome in adults and children is usually caused by surgery. This surgery may be done to address Crohn's disease, *volvulus*, tumors, injury, necrotizing enterocolitis, bypass surgery to treat obesity, or surgery to remove otherwise diseased or damaged portions of the small intestine. Some children are also born with an abnormally short small intestine, known as congenital short bowel.

The length of the small intestine can vary greatly, from as short as 2.75 m (9.0 ft) to as long as 10.49 m (34.4 ft). On average it is about 6.1 m (20 ft). Due to this variation it is recommended that following surgery the amount of bowel remaining be specified rather than the amount removed. Short bowel syndrome usually develops when there is less than 2 meters (6.6 feet) of the small intestine left to absorb sufficient nutrients.

In a process called intestinal adaptation, physiological changes to the remaining portion of the small intestine occur to increase its absorptive capacity. These changes include enlargement and lengthening of the villi found in the lining, increase in the diameter of the small intestine and slowdown in peristalsis or movement of food through the small intestine.

As discussed above, symptoms of short bowel syndrome are usually addressed with medication. These include antidiarrheal medicine, vitamin, mineral supplements and L-glutamine powder mixed with water, H2 blocker and proton pump inhibitors to reduce stomach acid, and lactase supplement.

In 2004, the U.S. FDA approved a therapy that reduces the frequency and volume of total parenteral nutrition (TPN), comprising: NutreStore (oral solution of glutamine) and Zorbtive (growth hormone, of recombinant DNA origin, for injection) together with a specialized oral diet. In 2012, an advisory panel to the USFDA voted unanimously to approve for treatment of SBS the agent teduglutide, a glucagon-like peptide-2 analog developed by NPS Pharmaceuticals.

Surgical procedures to lengthen dilated bowel include the Bianchi procedure, where the bowel is cut in half and one end is sewn to the other, and a newer procedure called serial transverse enteroplasty (STEP), where the bowel is cut and stapled in a zigzag pattern. Heung Bae Kim, M D, and Tom Jaksic, M D, both of Children's Hospital Boston, devised the STEP procedure in the early 2000s. The procedure lengthens the bowel of children with SBS and may allow children to avoid the need for intestinal transplantation. As of June 2009, Kim and Jaksic have performed 18 STEP procedures. The Bianchi and STEP procedures are usually performed by pediatric surgeons at quaternary hospitals specializing in small bowel surgery.

In sum, there is no cure for short bowel syndrome except transplant. Although promising, small intestine transplant has a mixed success rate, with postoperative mortality rate of up to 30%. Otherwise, the-year and 4-year survival rate are 90% and 60%, respectively. In newborn infants, the 4-year survival rate on parenteral nutrition is approximately 70%. In newborn infants with less than 10% of expected intestinal length, 5 year survival is approximately 20%. Some studies suggest that much of the mortality is due to a complication of the total parenteral nutrition (TPN), especially chronic liver disease. Much hope is vested in Omegaven®, a type of lipid TPN feed, in which recent case reports suggest the risk of liver disease is much lower.

B. Formulations and Routes of Administration

Where treatment of diseases such as SBS are contemplated, it will be necessary to prepare pharmaceutical compositions of the disclosed EGF reagents in a form appropriate for the intended application. Generally, this will entail preparing compositions that are essentially free of pyrogens, as well as other impurities that could be harmful to humans or animals.

One will generally desire to employ appropriate salts and buffers to render reagents stable. Buffers also will be employed when recombinant cells are introduced into a patient. Aqueous compositions of the present disclosure comprise an effective amount of the reagent to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the reagents of the present disclosure, its use in therapeutic compositions is contemplated. Supplementary active ingredients also can be incorporated into the compositions.

The reagent of the present disclosure may include classic pharmaceutical preparations. Administration of these compositions according to the present disclosure will be via any common route so long as the target tissue is available via that route. Such routes include oral, nasal, buccal, rectal, vaginal or topical route. Alternatively, administration may be by orthotopic, intradermal, subcutaneous, intramuscular, intraperitoneal, or intravenous injection. Such compositions would normally be administered as pharmaceutically acceptable compositions, described supra.

The antibodies and constructs may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The reagents of the disclosure can be incorporated into pharmaceutical compositions suitable for administration to a subject. Typically, the pharmaceutical composition comprises a reagent of the disclosure and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the reagent.

The reagents of the disclosure can be incorporated into a pharmaceutical composition suitable for parenteral administration (e.g., intravenous, subcutaneous, intraperitoneal, intramuscular). The compositions of this disclosure may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application.

Supplementary active compounds can also be incorporated into the compositions. In certain embodiments, a reagent of the disclosure is co-formulated with and/or co-administered with one or more additional therapeutic agents that are useful for treating disorders. For example, a reagent according to the present disclosure may be co-formulated and/or co-administered with one or more additional drugs. Such combination therapies may advantageously utilize lower dosages of the administered therapeutic agents, thus avoiding possible toxicities or complications associated with the various monotherapies. It will be appreciated by the skilled practitioner that when the antibodies of the disclosure are used as part of a combination therapy, a lower dosage of reagent may be desirable than when the reagent alone is administered to a subject (e.g., a synergistic therapeutic effect may be achieved through the use of combination therapy which, in turn, permits use of a lower dose of the reagent to achieve the desired therapeutic effect.

The pharmaceutical compositions described herein may include a "therapeutically effective amount" or a "prophylactically effective amount" of a reagent of the disclosure. A "therapeutically effective amount" refers to an amount effective, at dosages and for periods of time necessary, to achieve the desired therapeutic result. A therapeutically effective amount of the reagent may vary according to factors such as the disease state, age, sex, and weight of the individual; and the ability of the reagent portion to elicit a desired response in the individual. A therapeutically effective amount is also one in which any toxic or detrimental effects of the reagent are outweighed by the therapeutically beneficial effects. A "prophylactically effective amount" refers to an amount effective, at dosages and for periods of time necessary, to achieve the desired prophylactic result.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

As will be recognized by those in the field, a "therapeutically effective amount" refers to an amount of such that, when provided to a subject in accordance with the disclosed and claimed methods effects one of the following biological activities: treatment of any aspect or symptom cancer or autoimmune disease.

As understood in the art, such therapeutically effective amount will vary with many factors including the age and weight of the patient, the patient's physical condition, the condition to be treated, and other factors. An effective amount of the disclosed compounds will also vary with the particular combination administered. However, typical doses may contain from a lower limit of about 1 µg, 5 µg, 10 µg, 50 µg to 100 µg to an upper limit of about 100 µg, 500 µg, 1 mg, 5 mg, 10 mg, 50 mg or 100 mg of the pharmaceutical compound per day. Also contemplated are other dose ranges such as 0.1 µg to 1 mg of the compound per dose. The doses per day may be delivered in discrete unit doses, provided continuously in a 24 hour period or any portion of that the 24 hours. The number of doses per day may be from 1 to about 4 per day, although it could be more. Continuous delivery can be in the form of continuous infusions. The terms "QID," "TID," "BID" and "QD" refer to administration 4, 3, 2 and 1 times per day, respectively. Exemplary doses and infusion rates include from 0.005 nmol/kg to about 20 nmol/kg per discrete dose or from about 0.01/pmol/kg/min to about 10 pmol/kg/min in a continuous infusion. These doses and infusions can be delivered by intravenous administration (i.v.) or subcutaneous administration (s.c.). Exemplary total dose/delivery of the pharmaceutical composition given i.v. may be about 2 µg to about 8 mg per day, whereas total dose/delivery of the pharmaceutical composition given s.c. may be about 6 µg to about 6 mg per day.

The disclosed compounds may be administered, for example, at a daily dosage of, for example: from about 0.01 mg/kg to about 100 mg/kg; from about 0.01 mg/kg to about 80 mg/kg; from about 0.01 mg/kg to about 70 mg/kg; from about 0.01 mg/kg to about 60 mg/kg; from about 0.01 mg/kg to about 50 mg/kg; from about 0.01 mg/kg to about 40 mg/kg; from about 0.01 mg/kg to about 30 mg/kg; from about 0.01 mg/kg to about 25 mg/kg; from about 0.01 mg/kg to about 20 mg/kg; from about 0.01 mg/kg to about 15 mg/kg; from about 0.01 mg/kg to about 10 mg/kg; from about 0.01 mg/kg to about 5 mg/kg; from about 0.01 mg/kg to about 3 mg/kg; from about 0.01 mg/kg to about 1 mg/kg; from about 0.01 mg/kg to about 0.3 mg/kg from about 100 mg/kg to about 90 mg/kg; from about 100 mg/kg to about 80 mg/kg; from about 100 mg/kg to about 70 mg/kg; from about 100 mg/kg to about 60 mg/kg; from about 100 mg/kg to about 50 mg/kg; from about 100 mg/kg to about 40 mg/kg; from about 85 mg/kg to about 10 mg/kg; from about 75 mg/kg to about 20 mg/kg; from about 65 mg/kg to about 30 mg/kg; from about 55 mg/kg to about 35 mg/kg; or from about 55 mg/kg to about 45 mg/kg. Administration may be by injection of a single dose or in divided doses.

The term "unit dose" refers to a physically discrete unit suitable for use in a subject, each unit containing a predetermined quantity of the composition calculated to produce the desired response in association with its administration, i.e., the appropriate route and treatment regimen. The quantity to be administered, both according to number of treatments and unit dose, depends on the subject to be treated, the state of the subject, and the protection desired. Precise amounts of the therapeutic composition also depend on the judgment of the practitioner and are peculiar to each individual.

C. Combination Therapy

In another embodiment, the reagents of the present disclosure may be used in combination with other agents to improve or enhance the therapeutic effect of either. This process may involve administering both agents to the patient at the same time, either as a single composition or pharmacological formulation that includes both agents, or by administering two distinct compositions or formulations, wherein one composition includes an inhibitor of the present disclosure and the other includes the second agent(s).

The therapy of the present disclosure also may precede or follow the second agent treatment by intervals ranging from minutes to weeks. In embodiments where the other agent and the inhibitor of the present disclosure are administered separately, one may prefer that a significant period of time did not expire between each delivery, such that the agent and present inhibitor would still be able to exert an advantageously combined effect. In such instances, it is contemplated that one may administer both modalities within about 12-24 hours of each other and, more preferably, within about 6-12 hours of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. In other embodiments, it may be desirable to alternate the compositions so that the subject is not tolerized.

Various additional combinations may be employed, wherein the reagent of the present disclosure is "A" and the secondary agent is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

It is expected that the treatment cycles would be repeated as necessary. Suitable combination therapies for SBS are described elsewhere in this document.

III. EXAMPLES

The following examples are included to demonstrate preferred embodiments of the disclosure. It should be appreciated by those of skill in the art that the techniques disclosed in the examples which follow represent techniques discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1: Methods

Instrumentation and General Methods

Commercially available reagents and solvents were used without further purification unless stated otherwise. LC-MS analyses of synthetic intermediates were performed on an Agilent 1100 electrospray mass spectrometer in positive ion mode with scan range was 100-1000d. Preparative normal phase chromatography was performed on a CombiFlash Rf+ (Teledyne Isco) with pre-packed RediSep Rf silica gel cartridges. Preparative reverse phase HPLC was performed on a CombiFlash Rf+(Teledyne Isco) equipped with RediSep Rf Gold pre-packed C18 cartridges and an acetonitrile/water/0.05% TFA gradient unless stated otherwise. The retention time and purity of tested compounds was ≥90% as determined by HPLC analysis conducted on an Agilent 1100 system with diode array detector using an Ascentis Express Peptide ES-C18 2.7 micron, 30×4.6 mm reverse phase C18 column, using a 5 to 95% acetonitrile/water/0.05% TFA gradient over 3 min at 2.5 mL/min unless stated otherwise. NMR spectra were recorded on a Bruker 400 MHz spectrometer. The signal of the deuterated solvent was used as internal reference. Chemical shifts (δ) are given in ppm and are referenced to residual not fully deuterated solvent signal. Coupling constants (J) are given in Hz. MALDI-QIT-TOF mass spectrometry was used for identification and characterization of the recombinant protein products on a Shimadzu Axima Resonance instrument. Aqueous samples were desalted using Millipore ZipTips™ eluted with 20 mg/mL dihydroxybenzoic acid (DHB) matrix in 50% acetonitrile/0.1% trifluoroacetic acid. Mass spectra of protein and protein conjugates were conducted on an Agilent QTOF 6550 LC/MS system with electrospray ionization for quantitation and accurate mass measurements with an Agilent 1200 HPLC and MassHunter software for instrument control and quantitation.

Example 2: Preparation of Fatty Acid Conjugation Reagents

SCHEME 1: Preparation of Fatty Acid Conjugation Reagent $C_{16}$COH-γGlu-OSu

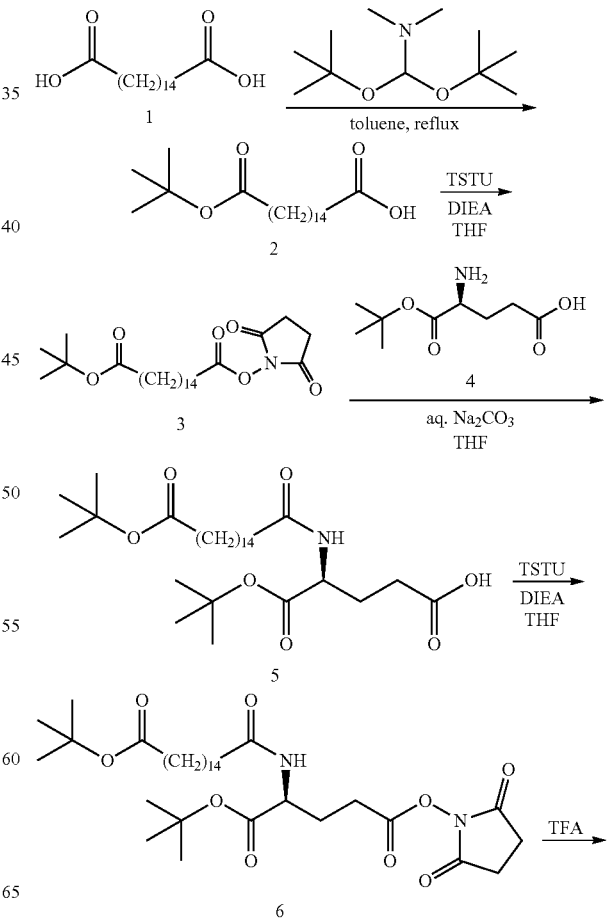

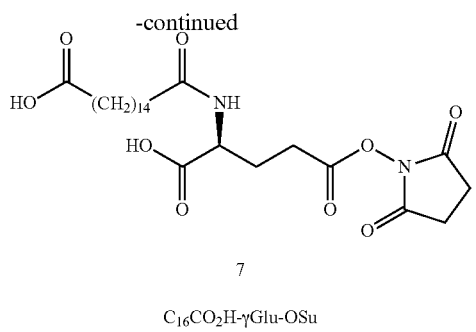

C<sub>16</sub>CO₂H-γGlu-OSu

Preparation of (S)-16-((1-carboxy-4-((2,5-dioxopyrrolidin-1-yl)oxy)-4-oxobutyl)amino)-16-oxohexadecanoic acid (7; $C_{16}CO_2H$-γGlu-OSu)

Step 1. 1,1-Di-tert-butoxy-N,N-dimethylmethanamine (5.0 mL, 21 mmol) was added slowly dropwise via addition funnel to a refluxing mixture of hexadecanedioic acid (2.2 g, 7.7 mmol) in toluene (15 mL). After refluxing overnight, the mixture was concentrated and absorbed to 10 grams of silica gel and purified by flash chromatography (0 to 100% ethyl acetate/hexanes) to furnish 16-(tert-butoxy)-16-oxohexadecanoic acid (2) as a white solid (1.3 g, 3.8 mmol, 49% yield). LCMS m/z 365 (MH⁺).

Step 2. 16-(tert-butoxy)-16-oxohexadecanoic acid (2) (1300 mg, 3.80 mmol) was dissolved in THF (13 mL) and treated successively with DIEA (0.780 ml, 4.55 mmol), 1-hydroxypyrrolidine-2,5-dione (524 mg, 4.55 mmol), and O—(N-Succinimidyl)-N,N,N',N'-tetramethyluronium tetrafluoroborate (TSTU; 1371 mg, 4.55 mmol) and stirred overnight at room temp. The mixture was cooled to room temp and filtered, washing briefly with ethyl acetate. The filtrate was concentrated, diluted with ethyl acetate, washed with satd ammonium chloride (2×), satd NaHCO₃, and brine. The organic layer was dried over sodium sulfate, filtered and concentrated to give crude 1-(tert-butyl) 16-(2,5-dioxopyrrolidin-1-yl) hexadecanedioate (3) as a white solid (1535 mg, 3.49 mmol, 4:1 mixture of product and starting acid). LCMS m/z 462 (MNa⁺). Used as is in the next step.

Step 3. Crude 1-(tert-butyl) 16-(2,5-dioxopyrrolidin-1-yl) hexadecanedioate (3) (1.54 g, 3.49 mmol), L-Glu(OH)-t-butyl ester (ChemImpex; 710 mg, 3.49 mmol), and DIEA (0.658 mL, 3.84 mmol) in NMP (20 mL) was stirred at 50° C. for 2 h. The reaction was cooled to room temp and poured into satd NH₄Cl and extracted with ethyl acetate twice. The org layers were washed with satd NH₄Cl and brine, dried over sodium sulfate and concentrated to give (S)-5-(tert-butoxy)-4-(16-(tert-butoxy)-16-oxohexadecanamido)-5-oxopentanoic acid (5) as a clear oil (2.11 g; ~90% pure; contains NMP). LCMS m/z 550 (MNa⁺). Used as is in the next step.

Step 4. (S)-5-(tert-butoxy)-4-(16-(tert-butoxy)-16-oxohexadecanamido)-5-oxopentanoic acid (5) (2.11 g, 4.00 mmol) was dissolved in THF (20 mL) and treated successively with DIEA (0.821 mL, 4.8 mmol), and TSTU (1.44 g, 4.80 mmol) and stirred overnight at room temp. The mixture was diluted with diethyl ether and filtered, washing the ppt with ether. The filtrate was concentrated and purified by silica chromatography (0-50% EtOAc/hex) to give a clear oil which solidified under high vacuum to give 1-(tert-butyl) 5-(2,5-dioxopyrrolidin-1-yl) (16-(tert-butoxy)-16-oxohexadecanoyl)-L-glutamate (6) as a white solid (1.61 g, 2.58 mmol, 64% yield). LCMS m/z 647 (MNa⁺).

Step 5. 1-(tert-butyl) 5-(2,5-dioxopyrrolidin-1-yl) (16-(tert-butoxy)-16-oxohexadecanoyl)-L-glutamate (6) (410 mg, 0.656 mmol) was dissolved in TFA (2 mL) and stirred at room temp for 1 h. The TFA was evaporated. The residue was dissolved in DCM (5 mL), concentrated, and partitioned between ethyl acetate and brine. The ethyl acetate layer was dried over sodium sulfate and concentrated to give crude (S)-16-((1-carboxy-4-((2,5-dioxopyrrolidin-1-yl)oxy)-4-oxobutyl)amino)-16-oxohexadecanoic acid (7) as a white solid (298 mg, 0.581 mmol; ~80% pure). LCMS m/z 513 (MH⁺), 535 (MNa⁺); impurity is the hydrolyzed byproduct (15-carboxypentadecanoyl)-L-glutamic acid, m/z 416 (MH⁺), 438 (MNa⁺). Used as is.

Example 3: Expression and Purification of Gly-EGF Proteins

Preparation of Gly-EGF

Gly-EGF

Synthetic DNA coding for hEGF with an N-terminal Gly (GNSDSECPLSHDGYCLHDGVCMYIEALDKY-ACNCVVGYIGERCQYRDLKWWELR (SEQ ID NO: 2)) was subcloned into pET32a(+) vector as an N-terminal thioredoxin fusion with a His6 tag for metal affinity purification, with a TEV protease recognition site for removal of fusion partner and affinity tag. The expression construct was placed into chemically competent Origami B (DE3) cells via heat shock, and transformants selected by antibiotic on LB agar plates (100 ug/mL carbenicillin). After cell growth and induction, the soluble fraction from the Origami B E. coli host strain was applied to a Co++ metal affinity column. After elution of the thioredoxin-EGF fusion protein with imidazole, TEV protease cleavage was used to remove the thioredoxin and His6 tags from rhEGF. This cleavage reaction mixture was reapplied to a reequilibrated Co++ column and the unbound fraction containing mature Gly-EGF was collected. Gly-EGF purity was analyzed by SDS-PAGE under reducing and non-reducing conditions, and by reversed-phase HPLC. MALDI-QIT-TOF was used to confirm the expected protein molecular mass. Observed m/z 6273, consistent with predicted 6279 minus 6H atoms from disulfide bridge formation). UV calculated yield: ~14 mg in 20 mL 20 mM HEPES, 100 mM NaCl, pH 7.9 (~0.7 mg/mL).

The buffer solution was aliquoted into 5-10 mL fractions, acidified with 50% TFA/water and purified by reverse phase HPLC (0% acetonitrile to 100% acetonitrile) on a Biotage 10 g C-18 HPBiosphere column. Pure fractions were lyophilized to give pure Gly-EGF as a white solid (14.8 mg). QTOF LCMS m/z 785.09, 897.11, 1046.46, 1255.55, 1569.19; deconvoluted to 6273.41 (M); calcd 6273.04.

Preparation of Gly-EGF$_{(K28R;K48R)}$

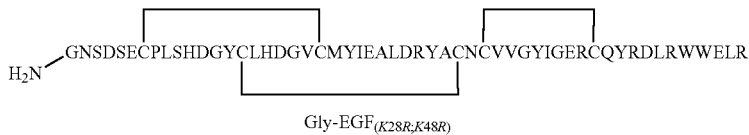

Gly-EGF$_{(K28R;K48R)}$

Gly-EGF$_{(K28R;K48R)}$ was prepared as described for Gly-EGF using synthetic DNA encoding GNSDSECPLSHDGY-CLHDGVCMYIEALDRYACNCVVGYIGER-CQYRDLRWWELR (SEQ ID NO: 3) wherein the K28 was mutated to R28 and K48 was mutated to R48. MALDI 6329.7 Da; theoretical 6329.0 Da. UV calculated yield: ~11.5 mg in 27 mL 20 mM HEPES, 100 mM NaCl, pH 7.9 (~0.43 mg/mL). The buffer solution was aliquoted into 5-10 mL fractions, acidified with 50% TFA/water and purified by reverse phase HPLC (0% acetonitrile to 100% acetonitrile) on a Biotage 10 g C-18 HPBiosphere column. Pure fractions were lyophilized to give pure Gly-EGF$_{(K28R;K48R)}$ as a white solid (12.3 mg). QTOF LCMS m/z 791.97, 905.11, 1055.80, 1266.75, 1583.19; deconvoluted to 6329.41 (M); calcd 6329.03.

Preparation of Gly-EGF$_{48}$

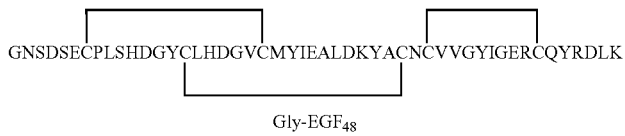

Gly-EGF$_{48}$

Gly-EGF$_{48}$ was prepared as described for Gly-EGF using synthetic DNA coding for GNSDSECPLSHDGY-CLHDGVCMYIEALDKYACNCVVGYIGERCQYRDLK (SEQ ID NO: 4) wherein the last 5 residues were truncated. MALDI 5502.81 Da; theoretical 5502 Da. UV calculated yield: ~7.1 mg in 4 mL 20 mM HEPES, 100 mM NaCl, pH 7.9 (~1.8 mg/mL).

Example 4: Preparation of Fatty Acid Conjugated EGF Proteins

Example 4A: Preparation of C16CO$_2$H-γGlu-Gly-EGF

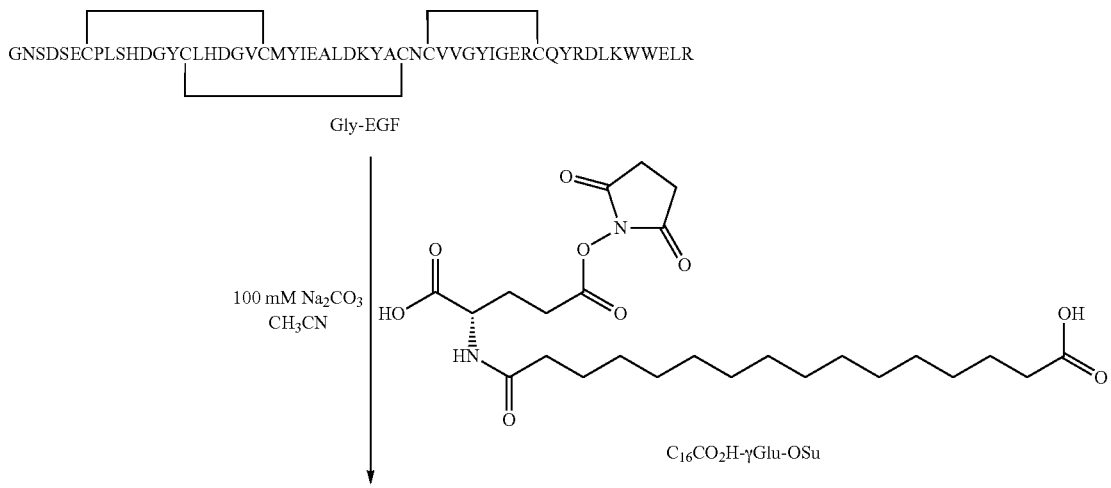

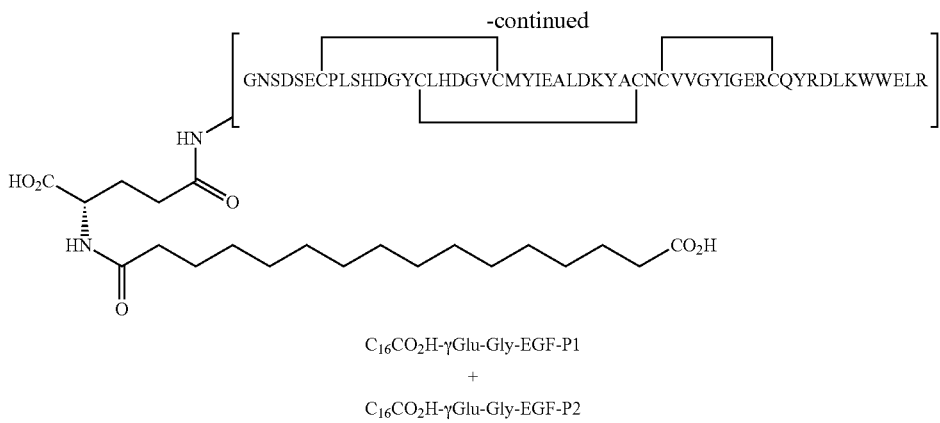

C₁₆CO₂H-γGlu-Gly-EGF-P1
+
C₁₆CO₂H-γGlu-Gly-EGF-P2

Gly-EGF (3.9 mg, 0.622 μmol) was dissolved in 150 μL 100 mM sodium carbonate buffer (pH 11.4). A suspension of (S)-16-((1-carboxy-4-((2,5-dioxopyrrolidin-1-yl)oxy)-4-oxobutyl)amino)-16-oxohexadecanoic acid (C₁₆CO₂H-γGlu-OSu; 3 eq, 1.0 mg, 2.0 μmol) in acetonitrile (100μ) was added to the protein solution at room temp to give a biphasic mixture which was stirred rapidly. Another 100 μL of the C₁₆CO₂H-γGlu-OSu in acetonitrile suspension (~1 mg, 3 eq) was added at 1 h. After stirring at room temp 1.45 h, the reaction was quenched with water (~300μ) and acidified with 50% TFA/water and purified by reverse phase HPLC (5% acetonitrile to 100% acetonitrile/0.05% TFA) on a Biotage 10 g C-18 HPBiosphere column. Pure fractions were lyophilized to give C16CO₂H-γGlu-Gly-EGF-P1 ($t_R$=2.08 min; 0.7 mg) and C16CO₂H-γGlu-Gly-EGF-P2 ($t_R$=2.15 min; 1.2 mg) as white solids. HPLC purity ~90% for both products. QTOF LCMS m/z 953.86, 1112.66, 1334.99, 1668.50; deconvoluted to 6670.84 (M); calcd 6670.56 for both products.

Example 4B: Preparation of C₁₆CO₂H-γGlu-Gly-EGF$_{(K28R;K48R)}$

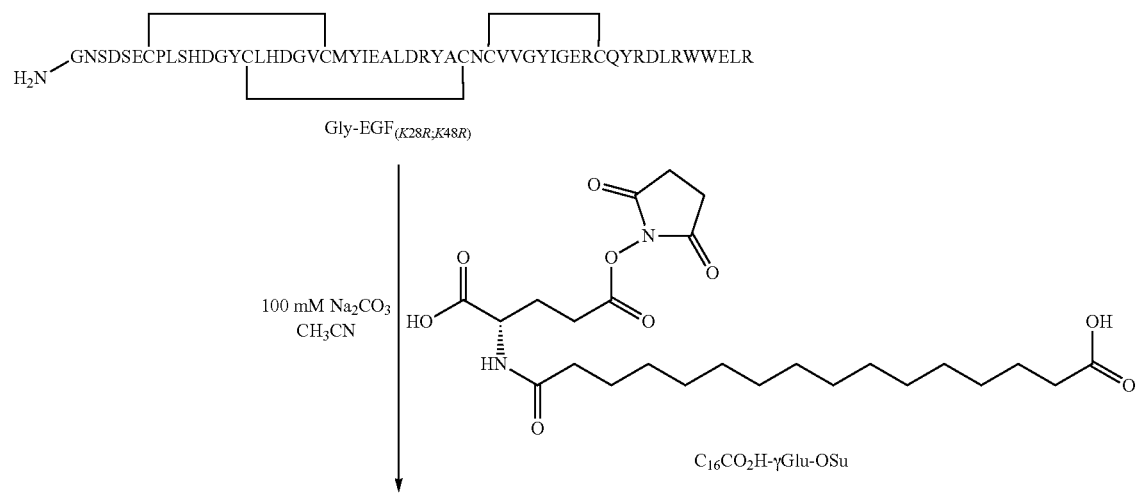

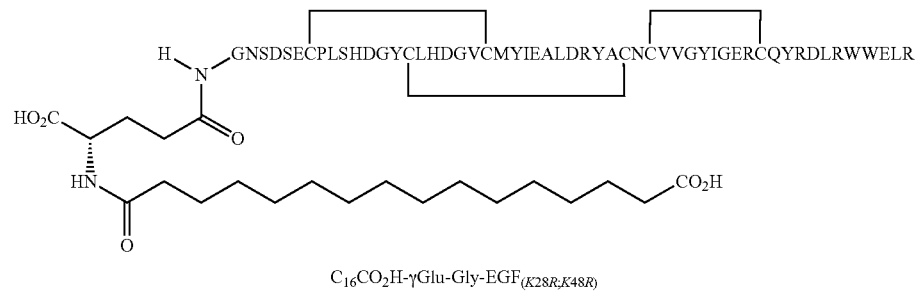

Gly-EGF$_{(K28R;K48R)}$ (4.1 mg, 0.622 μmop was dissolved in 150 μL 100 mM sodium carbonate buffer (pH 11.4). A suspension of (S)-16-((1-carboxy-4-((2,5-dioxopyrrolidin-1-yl)oxy)-4-oxobutyl)amino)-16-oxohexadecanoic acid (C$_{16}$CO$_2$H-γGlu-OSu; 3 eq, 1.0 mg, 2.0 μmol) in acetonitrile (100 μL) was added to the protein solution at room temp to give a biphasic mixture which was stirred rapidly. Another 100 μL of the C16CO$_2$H-γGlu-OSu in acetonitrile suspension (~1 mg, 3 eq) was added at 1 h. After 2 h, a third 1004 aliquot was added. After stirring overnight at room temp, the reaction was quenched with water (~300 μL) and acidified with 50% TFA/water and purified by reverse phase HPLC (5% acetonitrile to 100% acetonitrile/0.05% TFA) on a Biotage 10 g C-18 HPBiosphere column. Pure fractions were lyophilized to give C16CO$_2$H-γGlu-Gly-EGF$_{(K28R;K48R)}$ as a white solid (2.3 mg). HPLC purity >90%. QTOF LCMS m/z 841.75, 961.86, 1122.00, 1346.20, 1682.50; deconvoluted to 6727.04 (M); calcd 6726.54.

Example 5: Biological Data

Example 5A: EGFR Activation ELISA

EGF variants and their conjugates were tested in a commercial A431 epidermal carcinoma cell-based hEGF activity ELISA assay (R&D Systems; catalog #KCB1095). Briefly, the cell-based enzyme-linked immunosorbent assay (ELISA) kit contains the components required to run an ELISA using fluorogenic substrates to measure phosphorylated EGFR (Y1068) in whole cells. The phosphorylated EGFR antibody used in this kit does not cross-react with other phosphorylated tyrosine family members. Cells are grown in 96-well plates at 40,000 cells/well overnight, and stimulated with ligands for 10 minutes. Following stimulation, cells are fixed and permeabilized in the wells. The target protein phosphorylation is measured using a double immunoenzymatic labeling procedure. The cells are simultaneously incubated with a phospho-specific antibody and a normalization antibody. Two secondary antibodies are labeled with either horseradish-peroxidase (HRP) or alkaline phosphatase (AP), and two spectrally distinct fluorogenic substrates for either HRP or AP are used for detection. The fluorescence of the phosphorylated protein is normalized in each well for the correction of well-to-well variations. This two-wavelength assay results in precise analysis of protein phosphorylation with good reproducibility (R&D Systems). Results for Example 5A are shown in FIG. 1.

Example 5B: EGF Concentration ELISA

Figure 2:
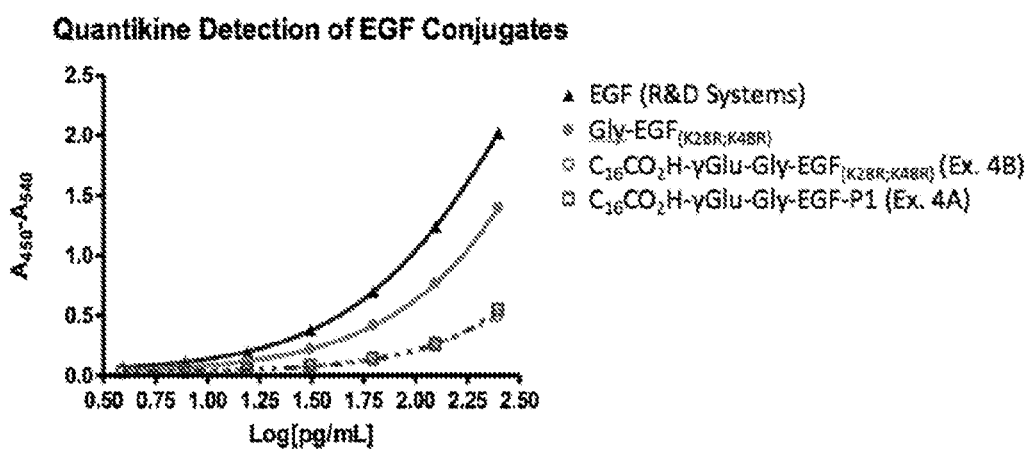
FIG. 2—Detection of EGF by commercial native EGF antibody ELISA kit.

EGF variants and their conjugates from both production and in vivo PK studies were tested in a commercial quantitative sandwich enzyme immunoassay technique (R&D Systems Quantikine ELISA Human EGF Immunoassay, cat. #DEG00) to determine concentration. Briefly, a monoclonal antibody specific for human EGF has been pre-coated onto a microplate. Standards and samples are pipetted into the wells and any EGF present is bound by the immobilized antibody. After washing away any unbound substances, an enzyme-linked polyclonal antibody specific for human EGF is added to the wells. Following a wash to remove any unbound antibody-enzyme reagent, a substrate solution is added to the wells and color develops in proportion to the amount of EGF bound in the initial step. The color development is stopped and the intensity of the color is measured. EGF concentration of samples are determined from a standard curve. Results for Example 5B are shown in FIG. 2.

Example 5C: In Vivo Half Life

Figure 3:
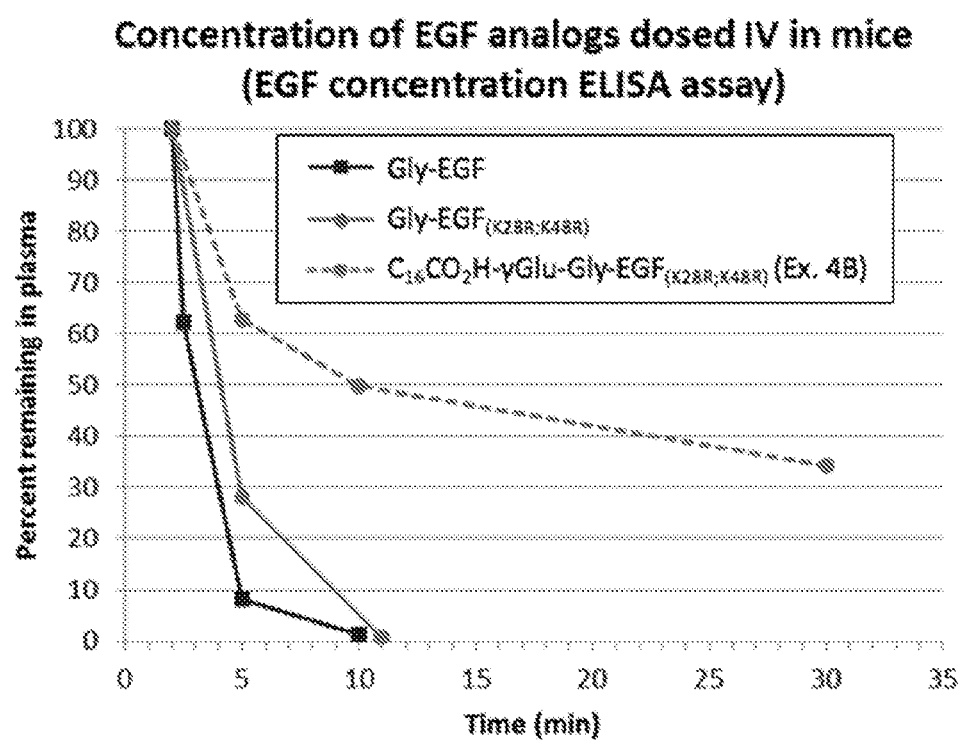
FIG. 3—Concentration of EGF variants and corresponding fatty acid conjugate Example 4B dosed IV in mice.

The in vivo half-life of fatty-acid conjugated EGF variants was determined in mice.CD1 mice received a 100 μg/kg IV dose of Gly-EGF$_{(K28R;K48R)}$ or C$_{16}$CO$_2$H-γGlu-Gly-EGF$_{(K28R;K48R)}$. Blood samples were collected at various time points between 2 minutes and 30 minutes. Samples were immediately treated with a protease inhibitor cocktail and anticoagulant. Blood was centrifuged at 1000×g for 10 minutes. The plasma supernatant was then centrifuged at 10,000×g to create platelet-poor plasma. Platelet-poor plasma samples were then stored at −80° C. until analysis by the aforementioned EGF activity ELISA and/or the EGF concentration ELISA assay. Results using the EGF Concentration ELISA (Example 5B) for Example 5C are shown in FIG. 3.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims

IV. REFERENCES

The following references, to the extent that they provide exemplary procedural or other details supplementary to those set forth herein, are specifically incorporated herein by reference.

Greene & Wuts, *Protective Groups in Organic Synthesis,* 3rd Ed., John Wiley, 1999.
*Handbook of Pharmaceutical Salts: Properties, and Use,* Stahl and Wermuth (Eds.), Verlag Helvetica Chimica Acta, 2002.
*March's Advanced Organic Chemistry: Reactions, Mechanisms, and Structure,* 2007. Reagan-Shaw et al., FASEB J., 22(3):659-661, 2008
Playford et al., *Gut* 39(2), 262-6, 1996.
McMellen et al., *Semin Pediatr Surg* 19:35-43, 2010.
Stem et al., *J Surg Res* 91, 38-42, 2009.
Sheng et al., *Am J Physiol Gastrointest Liver Physiol* 293, G599-606, 2007.
Chaet et al., *J Pedriatr Surg* 29, 1035-8, 1994.
Garg et al., *J Gastroenterol. Hepatol.,* 26(8):1221-1228, 2011.
LaRosa et al., *Pediatr. Transplant.,* 15(2):128-141, 2011.
Forbes, Matthew Herper, "Inside the pricing of a $300,000-a-year drug." www.forbes.com/sites/matthewherper/2013/01/03/inside-the-pricing-of-a-300000-a-year-drug/#7cc48d414917.
Sigalet et al., *J. Pediatr. Surg.,* 40:763-768, 2005.
Sullivan et al., *J Pediatr Surg,* 42:462-9, 2007.
Simpson et al., *Eur J Biochem,* 153:629-37, 1985.
Calnan et al., *Gut,* 47(5):622-7, 2000.

Gregory, *Regul Pept,* 22:217-26, 1988.
Ogiso et al., *Cell,* Vol. 110, 775-787, 2002
Campion et al., *Biochemistry,* 29, 9988-9993, 1990
Engler et al., *J Biol. Chem.,* 267:2274-2281, 1992
Tadaki and Niyogi, *J Biol. Chem.,* 268:10114-10119, 1993.

Savage et al., *J Biol. Chem.,* 247: 7612-7621, 1973.

Warner, *Cell Mol Gastroenterol Hepatol,* 2:429-438, 2016.
Carpenter and Cohen, *Ann. Rev. Biochem.,* 48:193-316, 1979.

---

What is claimed:
1. An EGF molecule further defined as:

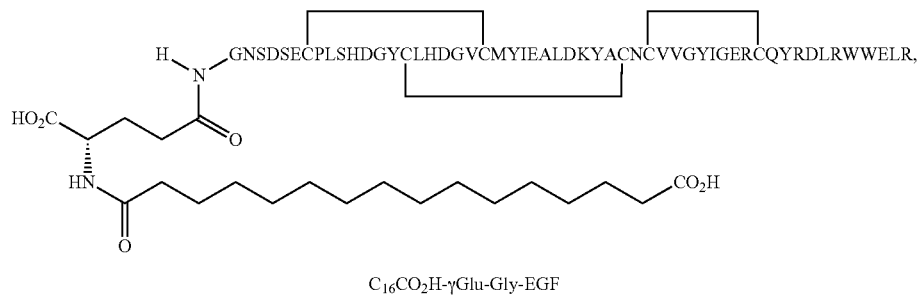

C₁₆CO₂H-γGlu-Gly-EGF

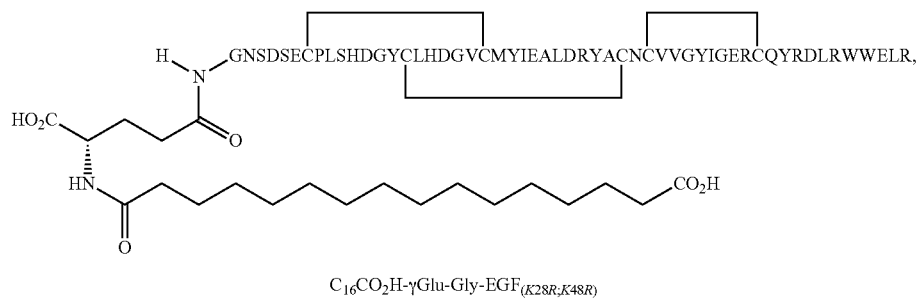

C₁₆CO₂H-γGlu-Gly-EGF$_{(K28R;K48R)}$

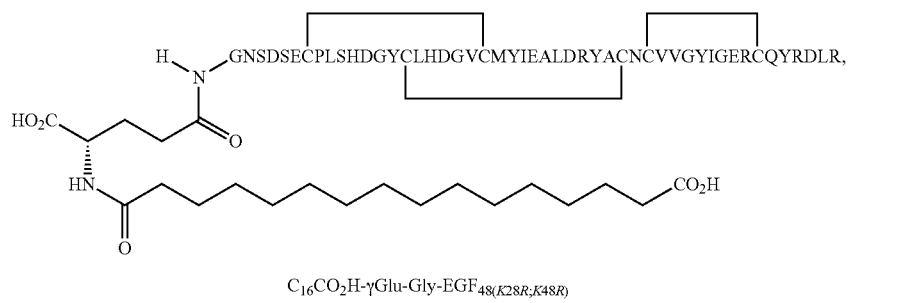

C₁₆CO₂H-γGlu-Gly-EGF$_{48(K28R;K48R)}$

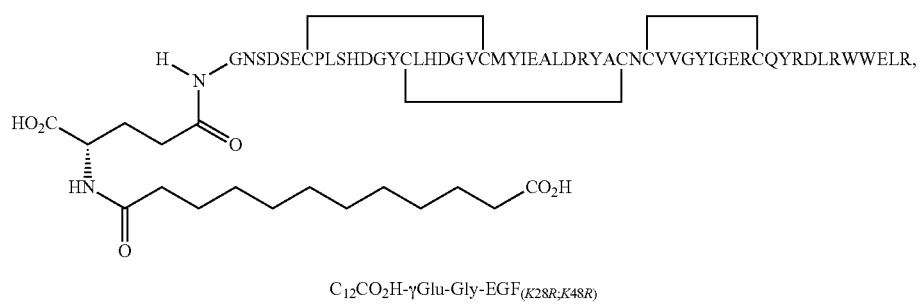

C₁₂CO₂H-γGlu-Gly-EGF$_{(K28R;K48R)}$

-continued
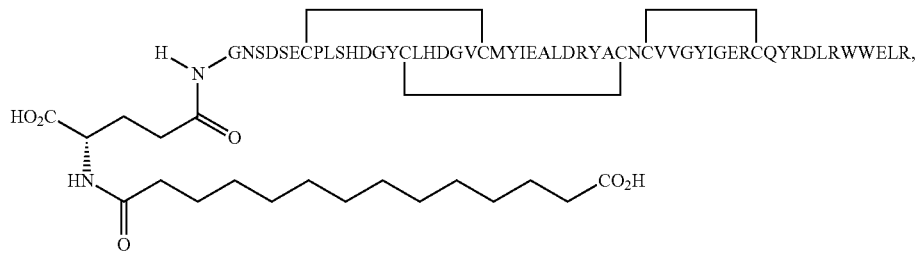
$C_{14}CO_2H$-γGlu-Gly-EGF$_{(K28R;K48R)}$
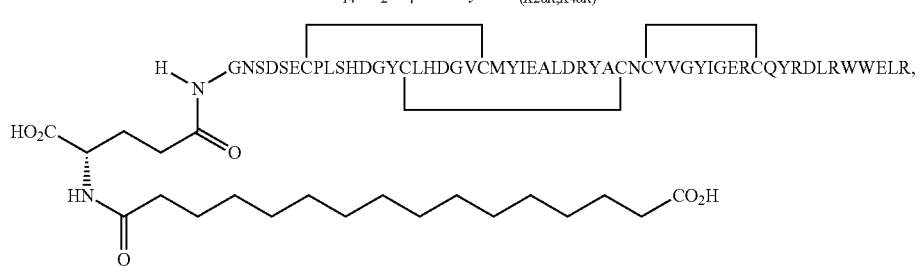
$C_{16}CO_2H$-γGlu-Gly-EGF$_{(K28R;K48R)}$
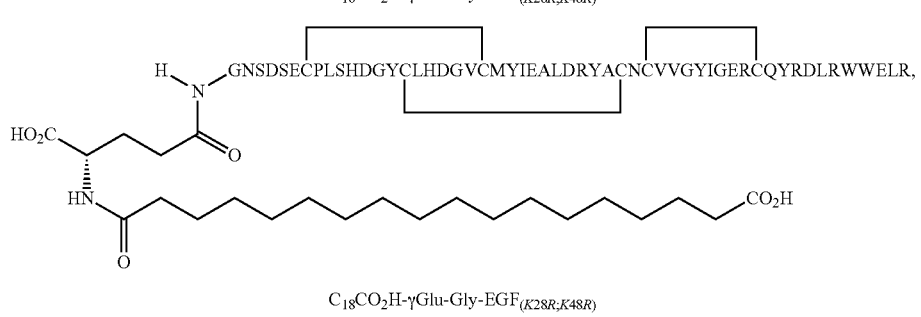
$C_{18}CO_2H$-γGlu-Gly-EGF$_{(K28R;K48R)}$
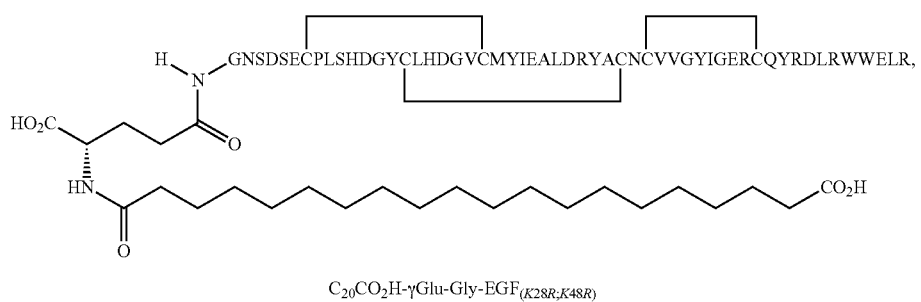
$C_{20}CO_2H$-γGlu-Gly-EGF$_{(K28R;K48R)}$
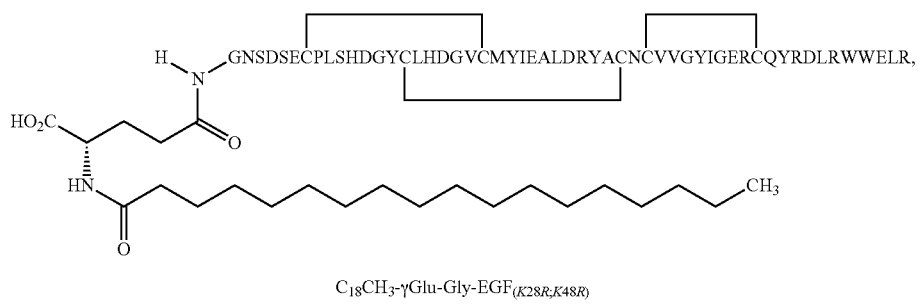
$C_{18}CH_3$-γGlu-Gly-EGF$_{(K28R;K48R)}$ -continued
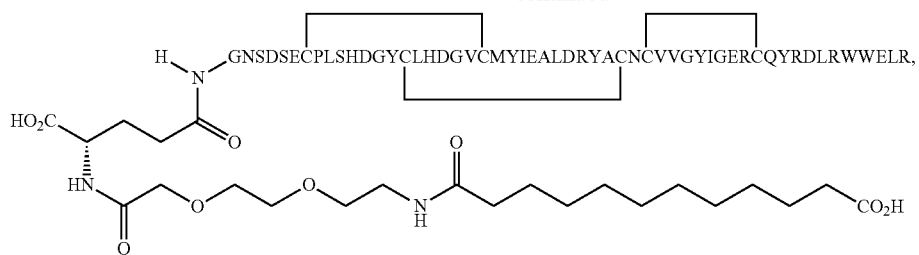
C$_{12}$CO$_2$H-AEEA-γGlu-Gly-EGF$_{(K28R;K48R)}$
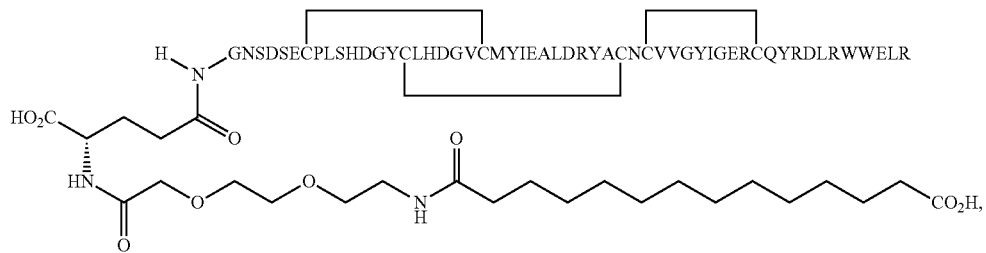
C$_{14}$CO$_2$H-AEEA-γGlu-Gly-EGF$_{(K28R;K48R)}$
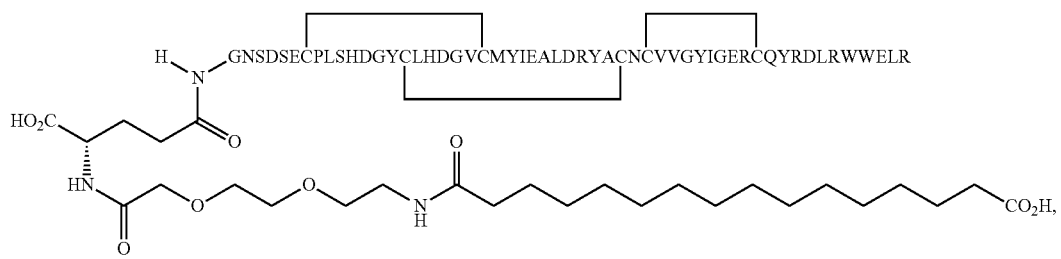
C$_{16}$CO$_2$H-AEEA-γGlu-Gly-EGF$_{(K28R;K48R)}$
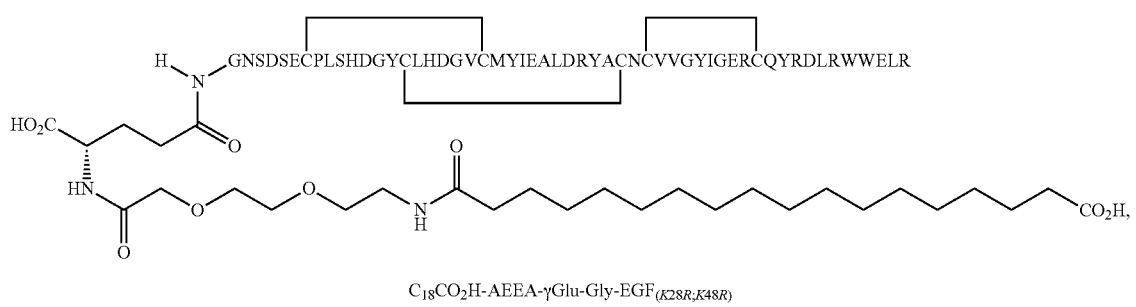
C$_{18}$CO$_2$H-AEEA-γGlu-Gly-EGF$_{(K28R;K48R)}$
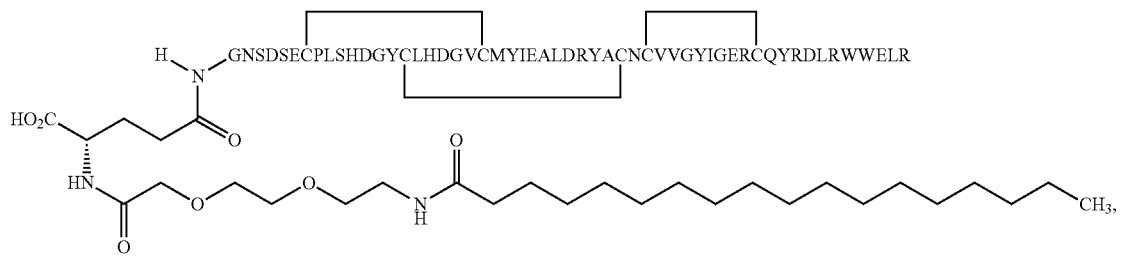
C$_{18}$CH$_3$-AEEA-γGlu-Gly-EGF$_{(K28R;K48R)}$

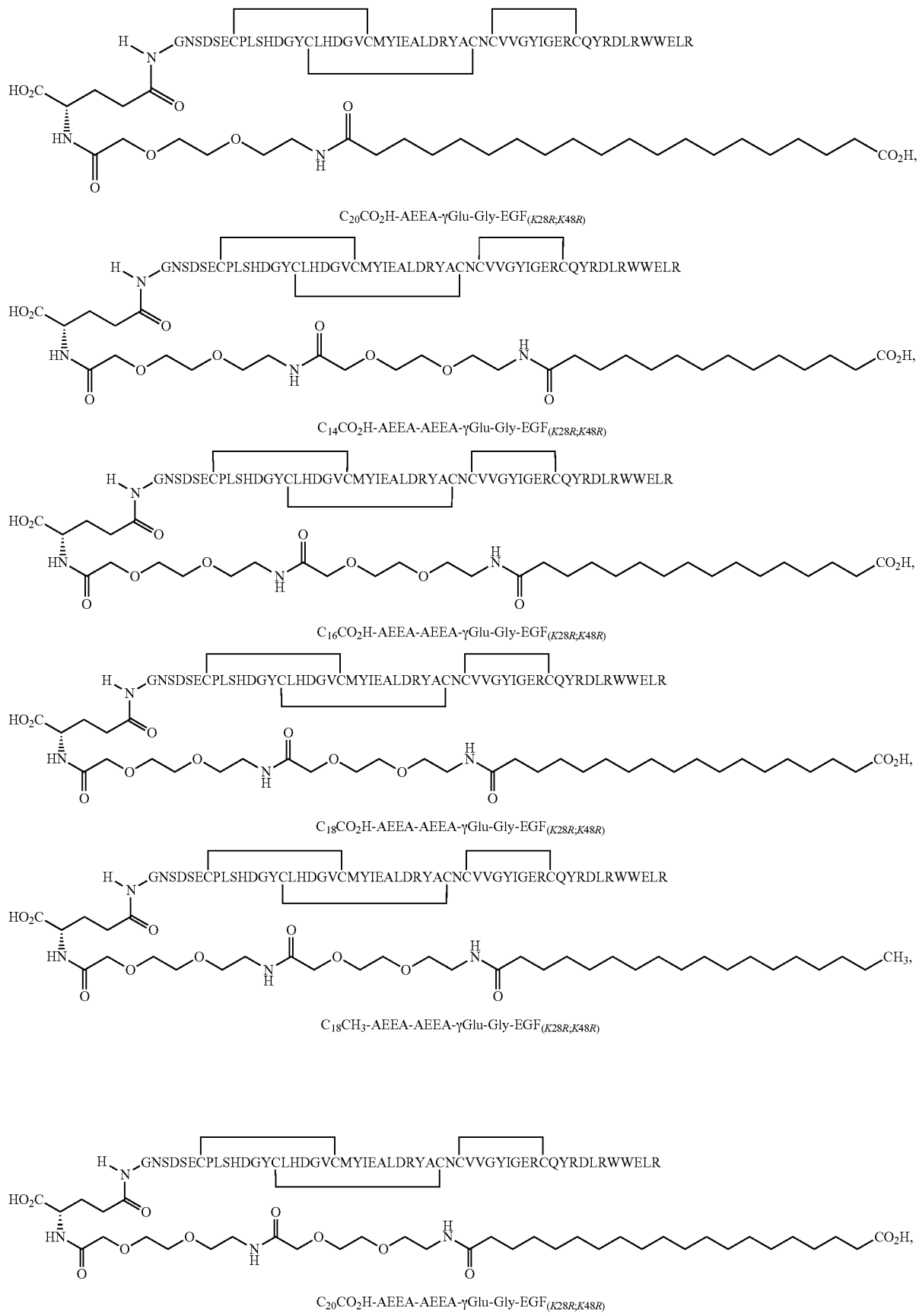

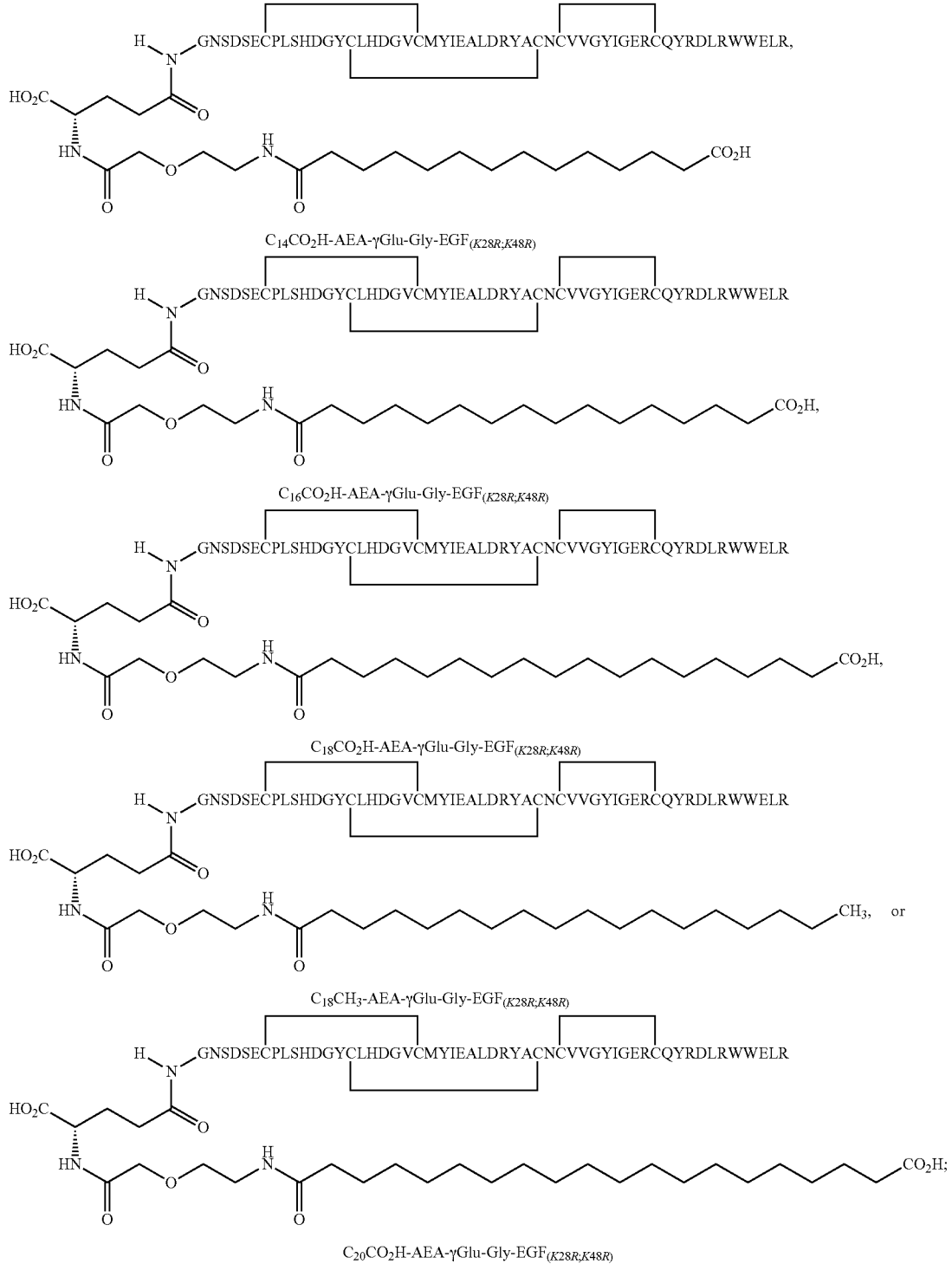
or a pharmaceutically acceptable salt thereof.
2. A pharmaceutical composition comprising:
(A) a EGF molecule of claim 1; and
(B) an excipient.